US010308959B2

United States Patent
Liu et al.

(10) Patent No.: US 10,308,959 B2
(45) Date of Patent: *Jun. 4, 2019

(54) METHODS, SYSTEMS, AND COMPOSITIONS RELATING TO MIRNA-146A

(71) Applicant: Henry Ford Health System, Detroit, MI (US)

(72) Inventors: Xianshuang Liu, Troy, MI (US); Zhenggang Zhang, Troy, MI (US); Michael Chopp, Southfield, MI (US); Lei Wang, Troy, MI (US); Benjamin A. L. Buller, Bloomfield Hills, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/600,567

(22) Filed: May 19, 2017

(65) Prior Publication Data

US 2017/0321225 A1  Nov. 9, 2017

Related U.S. Application Data

(63) Continuation-in-part of application No. 14/761,442, filed as application No. PCT/US2014/012532 on Jan. 22, 2014, now Pat. No. 9,670,490.

(60) Provisional application No. 61/754,279, filed on Jan. 18, 2013.

(51) Int. Cl.
| | | |
|---|---|---|
| C12N 15/113 | (2010.01) | |
| C12N 15/87 | (2006.01) | |
| A61K 31/7088 | (2006.01) | |
| C12N 5/079 | (2010.01) | |
| C12N 15/11 | (2006.01) | |
| A61K 31/7105 | (2006.01) | |
| A61K 35/12 | (2015.01) | |
| A61K 35/15 | (2015.01) | |
| A61K 35/30 | (2015.01) | |
| A61K 48/00 | (2006.01) | |
| C12N 15/00 | (2006.01) | |

(52) U.S. Cl.
CPC .......... *C12N 15/87* (2013.01); *A61K 31/7088* (2013.01); *A61K 31/7105* (2013.01); *A61K 35/12* (2013.01); *C12N 5/0618* (2013.01); *C12N 15/11* (2013.01); *C12N 15/113* (2013.01); *A61K 35/15* (2013.01); *A61K 35/30* (2013.01); *A61K 48/00* (2013.01); *C12N 15/00* (2013.01); *C12N 2310/14* (2013.01); *C12N 2310/141* (2013.01); *C12N 2320/31* (2013.01); *C12N 2320/32* (2013.01)

(58) Field of Classification Search
None
See application file for complete search history.

(56) References Cited

U.S. PATENT DOCUMENTS

| | | |
|---|---|---|
| 8,309,070 B2 | 11/2012 | Low et al. |
| 9,555,060 B2 | 1/2017 | Katakowski et al. |
| 9,670,490 B2 | 6/2017 | Liu et al. |
| 2006/0235005 A1 | 10/2006 | Goff |
| 2012/0021992 A1 | 1/2012 | Chopp et al. |
| 2017/0247708 A1 | 8/2017 | Katakowski et al. |

FOREIGN PATENT DOCUMENTS

| | | |
|---|---|---|
| WO | WO 2007/126386 A1 | 11/2007 |
| WO | WO 2009/147519 A1 | 12/2009 |
| WO | WO 2010/119256 A1 | 10/2010 |
| WO | WO 2011/057003 A2 | 5/2011 |
| WO | WO 2012/044783 A2 | 4/2012 |
| WO | WO 2013/124817 A2 | 8/2013 |

OTHER PUBLICATIONS

Alvarez-Erviti et al., "Delivery of siRNA to the mouse brain by systemic injection of targeted exosomes", Biotechnology, 29(4):341-347, 2011.
Baj-Krzyworzeka et al. "Tumour-derived microvesicles carry several surface determinants and mRNA of tumour cells and transfer some of these determinants to monocytes", Cancer Immunol Immunother, 55(7):808-818, 2006.
Cogswell J. et al. "Identification of miRNA changes in Alzheimer's disease brain and CSF yields putative biomarkers and insights into disease pathways", Journal of Alzheimer's Disease, vol. 14, No. 1, 2008, p. 27-41.
Galanis et al., "Clinical outcome of gliosarcoma compared with glioblastoma multiforme North Central Cancer Treatment Group results", Journal of Neurosurgery, 89(3): 425-430 1998 (Abstract).
Katakowski et al., "MiR-146b-5p Suppresses EGFR Expression and Reduces In Vitro Migration and Invasion of Glioma", Cancer Investigation, 28(10):1024-1030, 2010.
Katakowski et al., "Exosomes from marrow stromal cells expressing miR-146b inhibit glioma growth," Cancer Letters, 335(1):201-204, 2013.
Maes et al. "MicroRNA: implications for Alzheimer Disease and other human CNS disorders", Current Genomics, vol. 10, No. 3, 2009, pp. 154-168.

(Continued)

*Primary Examiner* — J. E. Angell
(74) *Attorney, Agent, or Firm* — Cooley LLP; Ivor R. Elrifi; Matthew Pavao

(57) ABSTRACT

Some embodiments comprise methods, systems, and compositions to promote, improve and/or increase neuronal differentiation, oligodendrocyte differentiation, or neurological outcome or function in a patient in need thereof. Some embodiments also comprise the administration a composition comprising a pharmaceutically effective amount of one or more of a group comprising microRNA-146a, exosomes comprising microRNA-146a, a promoter of microRNA-146a expression, a microRNA-146a thymosin beta 4, and a phosphodiesterase 5 inhibitor to treat neurological conditions, diseases, or injuries in mammals, including in human beings.

23 Claims, 27 Drawing Sheets

Specification includes a Sequence Listing.

(56) References Cited

OTHER PUBLICATIONS

Okada, "Gene Therapy with Vector-producing Multipotent Mesenchymal Stromal Cells", Yakugaku Zasshi, 130(11):1513-1518, 2010.

Parisi et al., "Dysregulated microRNAs in amyotrophic lateral sclerosis microglia modulate genes linked to neuroinflamrnation", Cell Death and Disease, p. 1-10, 4:e959, 2013.

Roccaro et al., "Stroma-Derived Exosomes Mediate Oncogenesis in Multiple Myeloma", Blood, 118(21):286, 2011, Abstract 625, 53$^{rd}$ Annual Meeting and Exposition of the American Society of Hematology (ASH), Dec. 10-13, 2011.

Valadi et al. "Exosome-mediated transfer of mRNAs and microRNAs is a novel mechanism of genetic exchange between cells", Nature Cell Biology, 9(6):654-659, 2007.

Wang, Li-Ling et al., "The potential role of microRNA•146 in Alzheimer's disease: Biomarker or therapeutic target?" Medical Hypotheses, 78:398-401, 2012.

Xia et al., "microRNA-146b inhibits glioma cell migration and invasion by targeting MMPs", Brain Research, 1269:158-165, 2009.

| Property | dm | db | db+exo miR-146a |
|---|---|---|---|
| Fiber diameter(μm) | 8.60±0.3 | 7.25±0.13## | 8.28±0.15** |
| Axon diameter(μm) | 5.00±0.11 | 4.44±0.08## | 4.84±0.08** |
| myelin thickness(μm) | 1.71±0.05 | 1.40±0.03## | 1.72±0.04** |
| g ratio (axon/fiber diameter) | 0.59±0.01 | 0.61±0.01# | 0.58±0.01** |

Values are mean ± SE. #$P<0.05$, ## $P<0.01$ versus dm group and **$P<0.01$ versus db group. n = 8/group.

SEQUENCE LISTING

```
<160> NUMBER OF SEQ ID NOS: 18

<210> SEQ ID NO 1
<211> LENGTH: 22
<212> TYPE: RNA
<213> ORGANISM: Artificial Sequence
<220> FEATURE:
<223> OTHER INFORMATION: MicroRNA-146a

<400> SEQUENCE: 1
ugagaacuga auuccauggg uu                                              22

<210> SEQ ID NO 2
<211> LENGTH: 43
<212> TYPE: PRT
<213> ORGANISM: Homo sapiens

<400> SEQUENCE: 2

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40

<210> SEQ ID NO 3
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n = inosine
<220> FEATURE:
<221> NAME/KEY: misc_feature
<222> LOCATION: (13)..(13)
<223> OTHER INFORMATION: n = inosine

<400> SEQUENCE: 3
tactncggct ggntcctgac                                                 20
```

```
<210> SEQ ID NO 4
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n = inosine
<220> FEATURE:
<221> NAME/KEY: misc_feature
<222> LOCATION: (13)..(13)
<223> OTHER INFORMATION: n = inosine

<400> SEQUENCE: 4
gcctncccgt agncacaaaa                                              20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
atggcatcac agaagagacc ctca                                         24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
taaagaagcg cccgatggag tcaa                                         24

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
atgacgaaat gaccggctac                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
acaacgttct tccggtcaac                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gctgaacaaa gggagagacg                                              20
```

```
<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tgctttctcc ccaaattgac                                               20

<210> SEQ ID NO 11
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(2)
<223> OTHER INFORMATION: n = inosine
<220> FEATURE:
<221> NAME/KEY: misc_feature
<222> LOCATION: (8)..(8)
<223> OTHER INFORMATION: n = inosine

<400> SEQUENCE: 11
tncaatgncc acagatccga                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ctaaccaatt ccccatccct                                               20

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
gccattctgg tagaggaagt ttctc                                         25

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
cgccagtcca aaatcaagaa tc                                            22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tgaagcagag catgaccttg                                               20
```

```
<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cacaagaact gagtgggggt                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
cgcaaccagt caagttctca                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gaaaagtagc ccccaacctc                                              20
```

METHODS, SYSTEMS, AND COMPOSITIONS RELATING TO MIRNA-146A

CROSS-REFERENCE TO RELATED APPLICATIONS

This application is a continuation-in-part application of U.S. patent application Ser. No. 14/761,442, filed Jul. 16, 2015, which claims the benefit of and priority to PCT Application No. PCT/US2014/012532, filed on Jan. 22, 2014, which claims the benefit of and priority to U.S. Provisional Patent Application Ser. No. 61/754,279, filed Jan. 18, 2013, all of the aforementioned disclosures are hereby incorporated by reference in their entireties.

Government License Rights

This invention was made with government support under Grant Numbers R01 AG038658, R01 NS075156 and R01 AG037506 awarded by the National Institutes of Health. The government has certain rights in the invention.

SEQUENCE LISTING

This application incorporates by reference in its entirety the Sequence Listing entitled "25824-412469_ST25.txt" (4.25 KB), which was created on May 16, 2017, and filed electronically herewith.

TECHNICAL FIELD

Without limitation, some embodiments comprise methods, systems, and compositions relating to treatment of neurological conditions, disease, or injury, and the use of same in the research, diagnosis, and treatment of such conditions, disease, or injury.

BACKGROUND

Brain disease, injury, or damage, as some non-limiting examples, stroke and traumatic brain injury, often induces long term neurological deficits. Demyelination and remyelination are processes in which myelin sheaths are lost from around axons and later restored to demyelinated axons, respectively. These processes are involved in brain injury and in neurodegenerative diseases. Currently, there are no effective treatments available for improvement of neurological function after stroke, brain injury and neurodegenerative diseases.

Reduction of neurogenesis and loss of myelinating oligodendrocytes exacerbate neurological deficits. Diabetes affects an estimated 346 million people world-wide and the vast majority of diabetics have non-insulin-dependent type II diabetes. Peripheral neuropathy is one of the most common and disabling complications of diabetes mellitus. There is currently no effective treatment for preventing the development or reversing the progression of diabetic neuropathy.

SUMMARY

The following examples of some embodiments of the invention are provided without limiting the invention to only those embodiments described herein and without waiving or disclaiming any embodiments or subject matter:

Some embodiments provide methods, systems, and compositions for promoting, increasing, and/or improving neuronal differentiation, oligodendrocyte differentiation, and/or neurological outcome or function in a patient in need thereof, including in mammals, and specifically in human beings. Some embodiments comprise the administration of a composition comprising a pharmaceutically effective amount of one or more of a group comprising, or consisting of, microRNA-146a, a promoter of microRNA-146a expression, exosomes containing or enriched with microRNA-146a, a microRNA-146a mimic, thymosin beta 4, and a phosphodiesterase 5 inhibitor to a patient in need of treatment for a neurological condition, disease, or injury.

Some embodiments provide a medicament comprising a pharmaceutically effective amount of one or more of microRNA-146a, a promoter of microRNA-146a expression, exosomes containing or enriched with microRNA-146a, a microRNA-146a mimic, thymosin beta 4, and a phosphodiesterase 5 inhibitor, and/or use of such a medicament in treating a patient with respect to the patient's neurological condition, disease, or injury, including but not limited to, in conjunction with stroke.

BRIEF DESCRIPTION OF DRAWINGS

Some embodiments will now be described, by way of example only and without waiver or disclaimer of other embodiments, with reference to the accompanying drawings, in which:

DETAILED DESCRIPTION

Figure 1:
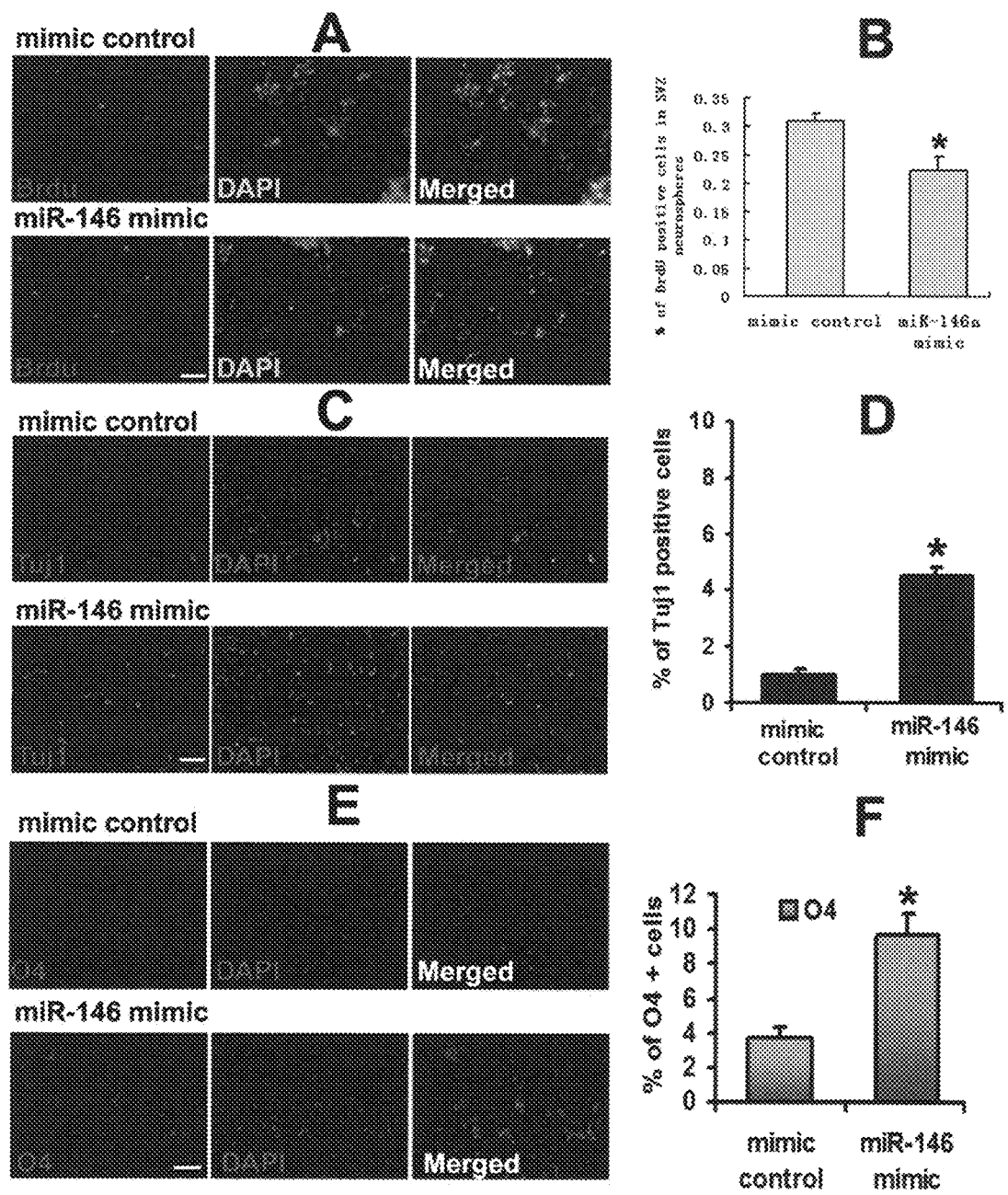
FIG. 1 is comprised of images and data representations showing the effect of miR-146a on proliferation and differentiation of neural progenitor cells.

The following examples of some embodiments of the invention are provided without limiting the invention to only those embodiments described herein and without waiving or disclaiming any embodiments or subject matter.

Some embodiments provide methods, systems, and compositions for promoting, increasing, and/or improving neuronal differentiation, oligodendrocyte differentiation, and/or neurological outcome or function, and/or the treatment, prevention and/or amelioration of one or more symptoms of a neurological disease, injury, disorder, or condition in a patient in need thereof, including in mammals, and specifically in human beings. Some embodiments comprise the administration of a composition comprising a pharmaceutically effective amount of one or more of a group comprising, or consisting of, microRNA-146a, exosomes containing or enriched in miR-146a, a promoter of microRNA-146a expression, a microRNA-146a mimic, thymosin beta 4, and a phosphodiesterase 5 inhibitor to a patient in need of prevention and/or treatment of a neurological condition, disease, or injury. As used herein, the term "microRNA 146a" is also referred to herein as "miR-146a" and "miRNA-146a", and are used interchangeably herein. Some embodiments provide a medicament comprising a pharmaceutically effective amount of one or more of microRNA-146a, exosomes containing or enriched in microRNA-146a, a promoter of microRNA-146a expression, a microRNA-146a mimic, thymosin beta 4, and a phosphodiesterase 5 inhibitor, and/or use of such a medicament in treating a patient with respect to the patient's neurological condition, disease, or injury, including but not limited to, in conjunction with stroke, traumatic brain injury, neuropathy, for example, peripheral neuropathy, diabetic neuropathy, Multiple Sclerosis, Parkinson's Disease, Alzheimer's Disease and other neurological diseases, injuries, disorders and conditions exemplified herein.

In accordance with some embodiments, without limitation, we have discovered unexpectedly that overexpression of microRNA-146a (SEQ ID NO: 1, UGA-GAACUGAAUUCCAUGGGUU) can therapeutically enhance neurogenesis (generation of new neurons) and oligodendrogenesis (generation of mature oligodendrocytes) and improve neurological outcome or function and therefore be useful in the treatment of neurological conditions, disease, and injury.

Some embodiments comprise the packaging of exosomes with one or more species of miRNA at high concentrations, for example, miR-146a, and these miRNAs are delivered into tissue in therapeutic doses. Packaged miRNAs can be those that are endogenous to the producing cells, but are forced to express at higher levels, or may be artificially designed miRNAs, introduced to suit the therapeutic need. Also, a combination of miRNAs can be packaged within the same exosomes.

In various embodiments, the present invention provides a method of preventing or treating a subject or patient suffering from a neurological disease, condition, disorder, or injury. The treatment comprises treating the patient in need thereof, with exosomes containing miR-146a microRNA, for example, exosomes enriched in miR-146a microRNA. In one embodiment, the method for preventing or treating a subject with a neurological disease, condition, disorder, or injury comprises administering a therapeutically effective amount of exosomes containing or enriched in microRNA-146a to the subject in need thereof.

In some related embodiments the neurological disease, condition, disorder, or injury comprises dementia; brain injury, for example, traumatic brain injury; neuropathy, for example, peripheral neuropathy; stroke or multiple sclerosis. In another embodiment, an exemplary method comprises the steps of: harvesting exosomes containing miR-146a microRNA from a cell population capable of producing exosomes containing miR-146a microRNA or media containing the cell population; and administering to the subject or patient in need thereof, the harvested exosomes in a pharmaceutically effective amount to treat the subject with the neurological disease condition, disorder, or injury. In some embodiments, the method optionally includes a step of confirming the presence of the miR-146a microRNA in the harvested exosomes.

In other embodiments, the present invention provides a method of treating a subject or patient suffering from a neurological disease, condition, disorder, or injury. The treatment comprises treating the patient in need thereof, with cells that are capable of producing exosomes containing miR-146a microRNA. The method comprises the steps of: providing a cell population capable of producing exosomes containing miR-146a; confirming the presence of the miR-146a microRNA in the cell population, and administering to the subject in need thereof, the cell population capable of producing exosomes containing miR-146a microRNA in a pharmaceutically effective amount to treat the subject with respect to the neurological disease or injury.

In some of these embodiments, the cells that are capable of producing exosomes containing miR-146a microRNA can include mammalian, for example, human: stem cells, mesenchymal stromal cells, umbilical cord cells, endothelial cells, for example, cerebral endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, and mastocytes. As used herein, stem cells, for example, can include stem cells from a mammalian subject, for example a human subject. In various embodiments, mammalian stem cells can include, without limitation, a progenitor cell, an embryonic stem cell, a pluripotent stem cell, an induced pluripotent stem cell, a hair follicle stem cell, a hematopoietic stem cell, a very small embryonic like stem cell, a mesenchymal stem cell, an endometrial regenerative cell (ERC), and a progenitor cell. In various embodiments, the cell population includes mesenchymal stem cells, mesenchymal stromal cells, and endothelial cells, for example, cerebral endothelial cells.

In various embodiments, methods of the present invention may utilize the above referenced cell populations that are derived from the subject to be treated, or they may be derived from a member of the same species, for example, the cells may be allogeneic.

In various embodiments, the exosomes may be administered to the patient in need thereof intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or stereotactically into neural tissue. In each of these administration modes, the exosomes or cell populations capable of producing such exosomes containing or enriched in miR-146a are administered to the subject in need thereof in accordance with standard medically approved methods.

In each of these embodiments, the exosomes may be administered in therapeutically effective amounts. The therapeutically effective amount of exosomes containing the miR-146a microRNA may be dependent on several factors known to those skilled in the art. The amount must be effective to achieve improvement, including but not limited to, decreased damage or injury, or improvement or elimination of one or more symptoms and other indicators as are selected as appropriate measures by those skilled in the art.

In some embodiments, neurological diseases, disorders, conditions and/or injuries that are beneficially treated, and/or prevented upon treatment with effective amounts of exosomes comprising miR146a, or cell population bearing exosomes comprising miR146a include, but are not limited to: stroke, brain injury, for example, traumatic brain injury (TBI), central pontine, dementia, multiple sclerosis (MS) (together with the similar diseases called idiopathic inflammatory demyelinating diseases), tumefactive multiple sclerosis, Solitary sclerosis, cognitive decline from aging, Alzheimer's disease, Parkinson's disease, epilepsy, migraine, neuropathy, for example, peripheral neuropathy, Vitamin B12 deficiency, myelinolysis, Tabes *Dorsalis*, transverse myelitis, Devic's neuromyelitis optica, fulminant or acute idiopathic inflammatory-demyelinating disease, Marburg variant of multiple sclerosis, Baló's concentric sclerosis, Schilder's disease, acute disseminated encephalomyelitis; transverse myelitis, optic neuritis, progressive multifocal leukoencephalopathy, acute hemorrhagic leukoencephalitis, acute disseminated encephalomyelitis, anti-myelin oligodendrocyte glycoprotein autoimmune encephalomyelitis, Leukodystrophy, adrenoleukodystrophy, adrenomyeloneuropathy, chronic inflammatory demyelinating polyradiculoneuropathy (CIDP), Guillain-Barre syndrome, chronic inflammatory demyelinating polyneuropathy, or anti-MAG peripheral neuropathy.

In some embodiments, the present invention provides a method of treating a subject suffering from dementia, neuropathy, brain injury, for example, traumatic brain injury, stroke or multiple sclerosis with exosomes containing miR-146a microRNA. In these exemplary methods, the steps may include: administering to the subject in need thereof, exosomes containing miR-146a microRNA or exosomes enriched with miR-146a microRNA in a pharmaceutically effective amount to treat the subject with the dementia, brain injury, neuropathy, stroke or multiple sclerosis. Optionally, the method for treatment also includes the steps of harvesting exosomes containing miR-146a microRNA from a cell population capable of producing the exosomes or media containing the cell population, and confirming the presence of the miR-146a microRNA in the harvested exosomes.

In each of these exemplary methods, the exosome producing cell population may include stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia; or mastocytes. As used herein, stem cells may include, a progenitor cell; a pluripotent stem cell, for example, an embryonic stem cell; an induced pluripotent stem cell; a hair follicle stem cell; a hematopoietic stem cell; a very small embryonic like stem cell; a mesenchymal stem cell; an endometrial regenerative cell (ERC); or a neural progenitor cell.

In these methods, the cells used to treat or ameliorate one or more symptoms associated with dementia, neuropathy, stroke or multiple sclerosis with exosomes containing miR-146a microRNA, the exosomes containing the miR-146a may be obtained from autologous cell populations. In various embodiments of the above referenced methods of treatment of dementia, neuropathy, stroke or multiple sclerosis with exosomes containing miR-146a microRNA, the exosomes may be administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or directly into neural tissue.

As used herein, it is believed that the oxygen deprivation (ischemia) and inflammation of the brain lead to several neurological diseases and injuries which may be chronic and/or acute. In some embodiments, neurological inflammation can progress to demyelination of neurons. Demyelination is the act of demyelinating, or the loss of the myelin sheath insulating the nerves. When myelin degrades, conduction of signals along the nerve can be impaired or lost, and the nerve eventually withers. This leads to certain neurodegenerative disorders like multiple sclerosis and chronic inflammatory demyelinating polyneuropathy.

Central nervous system (CNS) demyelination is a cause and consequence of a variety of neurological diseases and especially exemplified by MS and cognitive decline from aging, which follow a relapsing-remitting but then progressive course and a more protracted but progressive course, respectively. In both instances, these maladies involve increased oxidative stress (OS), which damages brain cells of oligodendrocyte lineage that are responsible for brain myelination, and production of myelination inhibitory factors including specific miRNAs.

According to an embodiment of the invention, the methods described herein are useful in inhibiting the development of and/or treating multiple sclerosis. Multiple sclerosis (MS), also known as "disseminated sclerosis" or "encephalomyelitis disseminata", is an inflammatory disease in which the fatty myelin sheaths around the axons of the brain and spinal cord are damaged, leading to demyelination and scarring as well as a broad spectrum of signs and symptoms. Disease onset usually occurs in young adults, and it is more common in women. It has a prevalence that ranges between 2 and 150 per 100,000.

Demyelination may also play an important role in the pathophysiology of traumatic brain injury. In experimental studies, brain injuries have been shown to be accompanied by a loss of myelin.

Neonatal brain disorders are also associated with demyelination and failure of remyelination. White matter injuries in the newborn brain, such as hypoxic ischemic encephalopathy and periventricular leukomalacia can result in cerebral palsy and cognitive disability. Failure of remyelination in such conditions contributes to permanent demyelinated lesions. Methods of the present invention are provided to treat, ameliorate and diminish any of the symptoms of ischemic tissue injury in the brain and the demyelination associated with brain diseases, disorders described above and below.

The present invention provides a method of treating or preventing a neurological disease or injury. In some embodiments, the neurological disease or injury is a disease or injury that results from direct trauma to the brain, an acute or chronic autoimmune insult, or an acute or chronic inflammation, either systemically, or locally in the brain. In some embodiments, the neurological disease or injury is treated upon administration of a therapeutically effective amount of exosomes containing miR-146a or cells from a cell population capable of producing exosomes containing miR-146a. In some of these embodiments, said patient is administered a therapeutically effective amount of exosomes containing miR-146a microRNA or cells from a cell population capable of producing exosomes containing miR-146a microRNA of the invention conjointly with an immune system suppressor, and/or an anti-inflammatory agent, for example, a glucocorticoid.

Exosomes containing miR-146a or cells from a cell population capable of producing exosomes containing miR-146a of the invention are capable of resolving, diminishing, ameliorating or improving a symptom associated with inflammation occurring in the brain of the subject, preferably a human subject. Glucocorticoids are also known for their role in treating inflammation. However, the full anti-inflammatory potential of glucocorticoids is often clinically constrained as a monotherapy due to the rate and severity of treatment-limiting adverse events that accompany high or prolonged dosing regimens. For example, the administration of glucocorticoids can result in side effects that mimic Cushing's disease. These side effects and others associated with glucocorticoid use include increased appetite and weight gain, deposits of fat in the chest, face, upper back, and stomach, water and salt retention leading to swelling and edema, high blood pressure, diabetes, slow healing of wounds, osteoporosis, cataracts, acne, muscle weakness, thinning of the skin, increased susceptibility to infection, stomach ulcers, increased sweating, mood swings, psychological problems such as depression, and adrenal suppression and crisis.

Advantageously, treatment of a subject in need thereof having a neurologic disease or injury with a combination of a glucocorticoid and exosomes containing miR-146a or cells from a cell population capable of producing exosomes containing miR-146a of the invention enhances the anti-inflammatory properties of both classes of agents while reducing the effects associated with high doses of glucocorticoids alone.

In methods of the invention, wherein a glucocorticoid is administered conjointly with exosomes containing miR-146a or cells from a cell population capable of producing exosomes containing miR-146a of the invention, the glucocorticoid may be chosen from any glucocorticoid known in the art. Glucocorticoids suitable for said conjoint administration include, but are not limited to, alclometasone, amcinonide, beclometasone, betamethasone, budesonide, ciclesonide, clobetasol, clobetasone, clocortolone, cloprednol, cortisone, cortivazol, deflazacort, desonide, desoximetasone, desoxycortone, dexamethasone, diflorasone, diflucortolone, difluprednate, fluclorolone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, prednylidene, rimexolone, tixocortol, triamcinolone, ulobetasol, mometasone, fluticasone propionate, beclomethasone dipropionate, fluocinolone, flunisolide hemihydrate, mometasone furoate monohydrate, desoxymethasone, diflorasone diacetate, hydrocortisone acetate, difluorocortolone, fluorocortisone, flumethasone, flunisolide, fluorocortolone, prednisolone, prednisone, cortisol, 6a-methylprednisolone, alclometasone dipropionate, fluclorolone acetonide, fluocinolone acetonide, betamethasone benzoate, fluocoritin butyl, betamethasone dipropionate, fluocortolone preparations, betamethasone valerate, fluprednidene acetate, flurandrenolone, clobetasol propionate, clobetasol butyrate, hydrocortisone, hydrocortisone butyrate, methylprednisolone acetate, diflucortolone valerate, flumethasone pivalate, or triamcinolone acetonide, or pharmaceutically acceptable salts thereof.

In certain embodiments, the patient to be treated by a method of the invention may already be receiving an anti-inflammatory drug (other than a glucocorticoid). In one preferred embodiment, the patient is already taking a glucocorticoid, such as one of the glucocorticoids described above, and will continue to take that drug conjointly with a composition comprising exosomes containing miR-146a or cells from a cell population capable of producing exosomes containing miR-146a of the invention. Alternatively, the exosomes containing miR-146a or cells from a cell population capable of producing exosomes containing miR-146a of the invention may be used as a replacement for the previously administered anti-inflammatory, anti-autoimmune or immune suppressing drug, for example, an anti-CD40L antibody, methotrexate, hydrocortisone, prednisone, prednisolone, methylprednisolone, betamethasone, VERIPRED™, ORAPRED™, triamcinolone acetonide, AVONEX™ (interferon beta-1a), BETASERON™ (interferon beta-1b), COPAXONE™ (glatiramer acetate), EXTAVIA™ (interferon beta-1b), GLATOPA™ (glatiramer acetate (Copaxone 20 mg dose)), PLEGRIDY™ (peginterferon beta-1a), REBIF™ (interferon beta-1a), ZINBRYTA™ (daclizumab) AUBAGIO™ (teriflunomide), GILENYA™ (fingolimod), AMPYRA® (Dalfampridine), TECFIDERA™ (dimethyl fumarate), LEMTRADA™ (alemtuzumab), NOVANTRONE™ (mitoxantrone), or TYSABRI™ (natalizumab), or alternatively, all of these anti-inflammatory, anti-autoimmune or immune suppressing drugs may be co-administered individually or in combination with a composition comprising exosomes containing miR-146a microRNA or cells from a cell population capable of producing exosomes containing miR-146a microRNA of the invention, either concurrently or sequentially to treat the neurologic disease or injury as exemplified herein.

In one embodiment, the method of treating or preventing a neurologic disease or injury according to this invention may comprise the additional step of conjointly administering to the patient another anti-inflammatory agent, such as, for example, a non-steroidal anti-inflammatory drug (NSAID), a mast cell stabilizer, or a leukotriene modifier.

In certain embodiments, the use of a composition comprising exosomes containing miR-146a or cells from a cell population capable of producing exosomes containing miR-146a of the invention and a glucocorticoid or other anti0-inflammatory agent in the treatment of a neurologic disease or injury does not preclude the separate but conjoint administration of another anti-inflammatory agent for example, a corticosteroid, a non-steroidal anti-inflammatory drug (NSAID), a mast cell stabilizer, or a leukotriene modifier.

In certain embodiments, the present invention provides a kit comprising: a) one or more single dosage forms of a composition containing exosomes containing miR-146a or cells from a cell population capable of producing exosomes containing miR-146a of the invention; and b) instructions for the administration of the exosomes containing miR-146a or cells from a cell population capable of producing exosomes containing miR-146a of the invention.

The present invention provides a kit comprising: a) a pharmaceutical formulation (e.g., one or more single dosage forms) comprising exosomes containing miR-146a or cells from a cell population capable of producing exosomes containing miR-146a of the invention; and b) instructions for the administration of the pharmaceutical formulation e.g., for treating or preventing a disorder or condition as discussed above, e.g., a neurologic disease or injury.

In certain embodiments, the kit further comprises instructions for the administration of the pharmaceutical formulation comprising exosomes containing miR-146a or cells from a cell population capable of producing exosomes containing miR-146a of the invention conjointly with a another immune system modulator, an anti-inflammatory agent, for example a corticosteroid, a non-steroidal anti-inflammatory drug (NSAID), a mast cell stabilizer, or a leukotriene modifier or combinations thereof as mentioned above. In certain embodiments, the kit further comprises a second pharmaceutical formulation (e.g., as one or more single dosage forms) comprising an immune system modulator, an anti-inflammatory agent, for example a corticosteroid, a non-steroidal anti-inflammatory drug (NSAID), a mast cell stabilizer, a leukotriene modifier, or a combinations thereof as mentioned above.

EXAMPLES

The following examples of some embodiments are provided without limiting the invention to only those embodiments described herein and without waiving or disclaiming any embodiments or subject matter.

Example 1

In accordance with some embodiments, without limitation, we have discovered unexpectedly that overexpression of microRNA-146a (also "miR-146a" or "miRNA-146a") (SEQ ID NO: 1, UGAGAACUGAAUUCCAUGGGUU) can therapeutically enhance neurogenesis (generation of new neurons) and oligodendrogenesis (generation of mature oligodendrocytes) and improve neurological outcome or function and therefore be useful in the treatment of neurological conditions, disease, and injury.

Some embodiments comprise the use of miR-146a in: 1) augmentation of newly generated neurons and oligodendrocytes leading to the improvement of neurological function after stroke, and 2) reduction of dorsal root ganglion neuron death leading to improvements of sensory conduction in diabetic peripheral neuropathy.

In accordance with some embodiments, we evaluated whether miR-146a affects adult neural stem cells to differentiate into neurons and oligodendrocytes. Primary neural stem cells isolated from the subventricular zone ("SVZ") of the lateral ventricle of the adult rat were employed. Using a neurosphere assay, we examined the effect of miR-146a on neural stem cell proliferation and differentiation. Neural stem cells were transfected with miR-146a mimics and cultured at a density of 10 cells/µl in growth medium for 3 days. Bromodeoxyuridine (BrdU, 30 µg/ml, Sigma Aldrich), the thymidine analog that is incorporated into the DNA of dividing cells during S-phase, was added 18 h prior to the termination of incubation. FIG. 1 shows the effect of miR-146a on proliferation and differentiation of neural progenitor cells. Panels A and B of FIG. 1 show BrdU immunoreactive cells after transfection with miRNA mimic controls and miR-146a mimics. Panels C-D and E-F show Tuj1 and O4, respectively, immunoreactive cells after transfection with miRNA mimic controls and miR-146a mimics. Scale bar=20 µm. N=3, p<0.05. We found that miR-146a mimics significantly (p<0.05) decreased the number of BrdU-positive cells (FIGS. 1A and B) compared to the cells transfected with miRNA mimic controls, indicating that exogenous miR-146a suppresses neural stem cell proliferation.

To evaluate the effect of miR-146a on neural stem cell differentiation, neural stem cells transfected with miR-146a mimics or mimic controls were cultured under differentiation media containing 2% fetal bovine serum without growth factors. Every 4 days, half of the medium was replaced with fresh medium. Incubation was terminated 10 days after plating. Immunostaining analysis revealed that introduction of miR-146a strikingly increased the percentage of Tuj1 (a marker of neuroblasts) positive cells (FIGS. 1C and D, n=3, p<0.05), but did not significantly affect the percentage of GFAP (a marker of astrocytes) positive cells compared with the cells transfected with mimic controls. In addition, transfection of miR-146a mimics increased the number of Oligodendrocyte 4 (O4) positive cells (FIGS. 1E and 1F), indicating that miR-146a induces neural stem cells to differentiate into neurons and oligodendrocytes.

Our work demonstrated that miR-146a promotes neuronal and oligodendrocyte differentiation of adult neural stem cells.

Figure 2:
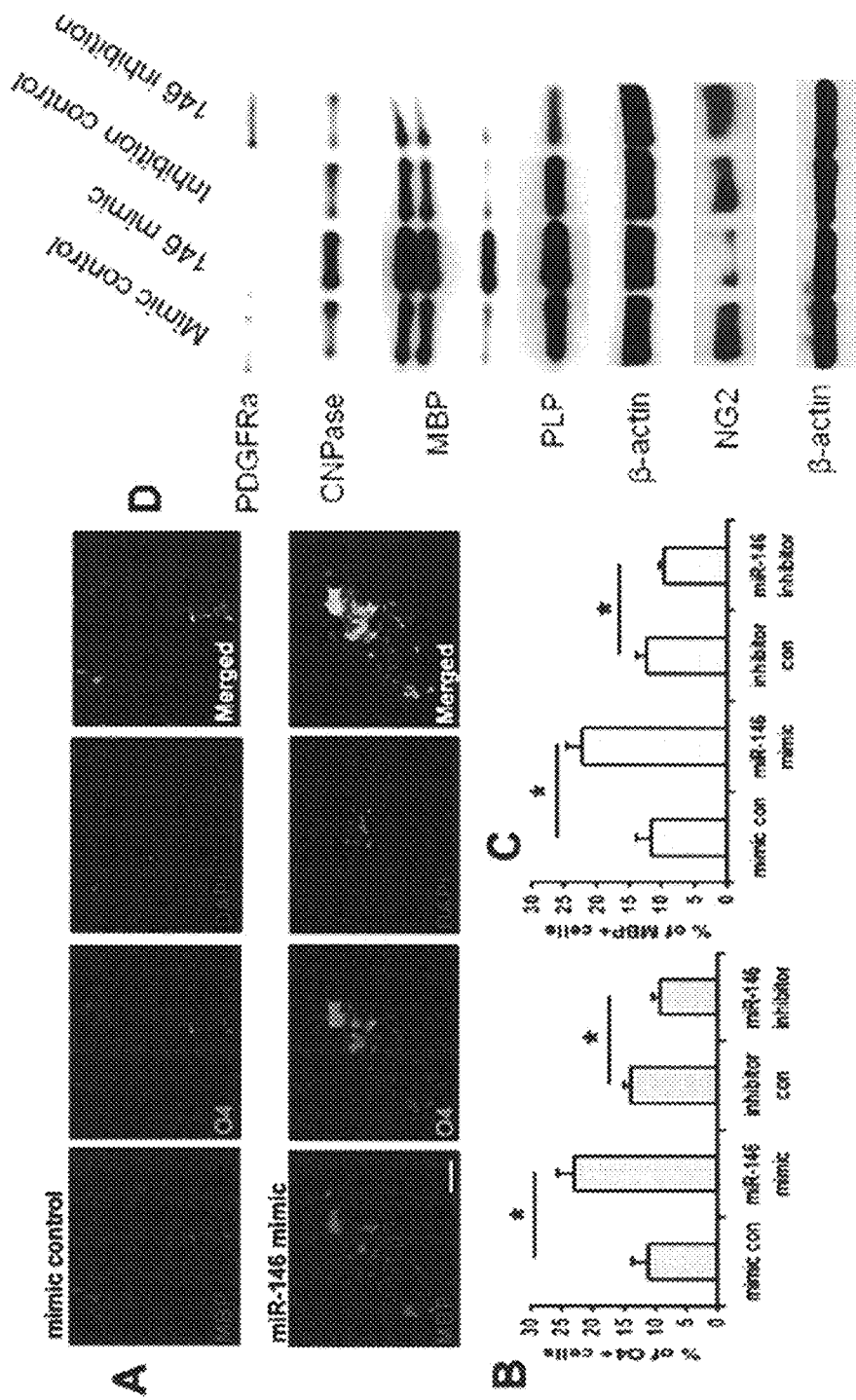
FIG. 2 is comprised of images and data representations showing the effect of miR-146a on differentiation of oligo-progenitor cells ("OPCs").

In addition to neural stem cells, oligodendrocyte progenitor cells ("OPCs") also differentiate into mature oligodendrocytes. We also examined the effect of miR-146a on OPC differentiation. OPCs isolated from embryonic day 18 rat embryos were used. We transfected OPCs with miR-146a mimics. FIG. 2 shows the effect of miR-146a on differentiation of OPCs. Immunocytochemistry (FIG. 2A) shows O4 and MBP positive cells in miRNA mimic control and miR-146a mimic groups. FIGS. 2B and C are quantitative data of O4 and MBP positive cells in different groups. FIG. 2D is Western blot data showing levels of CNPase, MBP, PLP, PDGFRα and NG2 in OPCs transfected with miRNA mimic control, miR-146a mimics, inhibitor control, and miR-146a inhibitor. β-actin was used as an internal control. *p<0.05, N=3/group. Scale bar=20 um. Immunocytochemistry analysis revealed that miR-146a mimics resulted in a significant increase in the number of myelin basic protein (MBP, a marker of mature oligodendrocytes) positive cells (FIGS. 2A-C). Furthermore, Western blot analysis showed that miR-146a mimics robustly increased protein levels of MBP, proteolipid protein ("PLP"), and 2', 3'-cyclic nucleotide 3'-phosphodiesterase ("CNPase"), all of them are markers of mature oligodendrocytes (FIG. 2D). In contrast, miR-146a mimics considerably decreased oligodendrocyte progenitor cell protein levels, PDGFRa and NG2 (FIG. 2D). Our results indicate that exogenous miR-146a promotes differentiation of oligodendrocyte progenitor cells into mature oligodendrocytes.

We also investigated the effect of endogenous miR-146a on oligodendrocyte maturation by transfecting OPCs with miRNA inhibitors. Attenuation of endogenous miR-146a significantly reduced the number of MBP+ cells (FIG. 2C). Western blot analysis showed that inhibition of miR-146a decreased protein levels of MBP, PLP and CNPase, but increased protein levels of PDGFRa and NG2 (FIG. 2D). Our observations indicate that endogenous miR-146a is required for oligodendrocyte maturation.

Collectively, our work demonstrated that miR-146a promotes OPCs to differentiate into mature oligodendrocytes.

Figure 3:
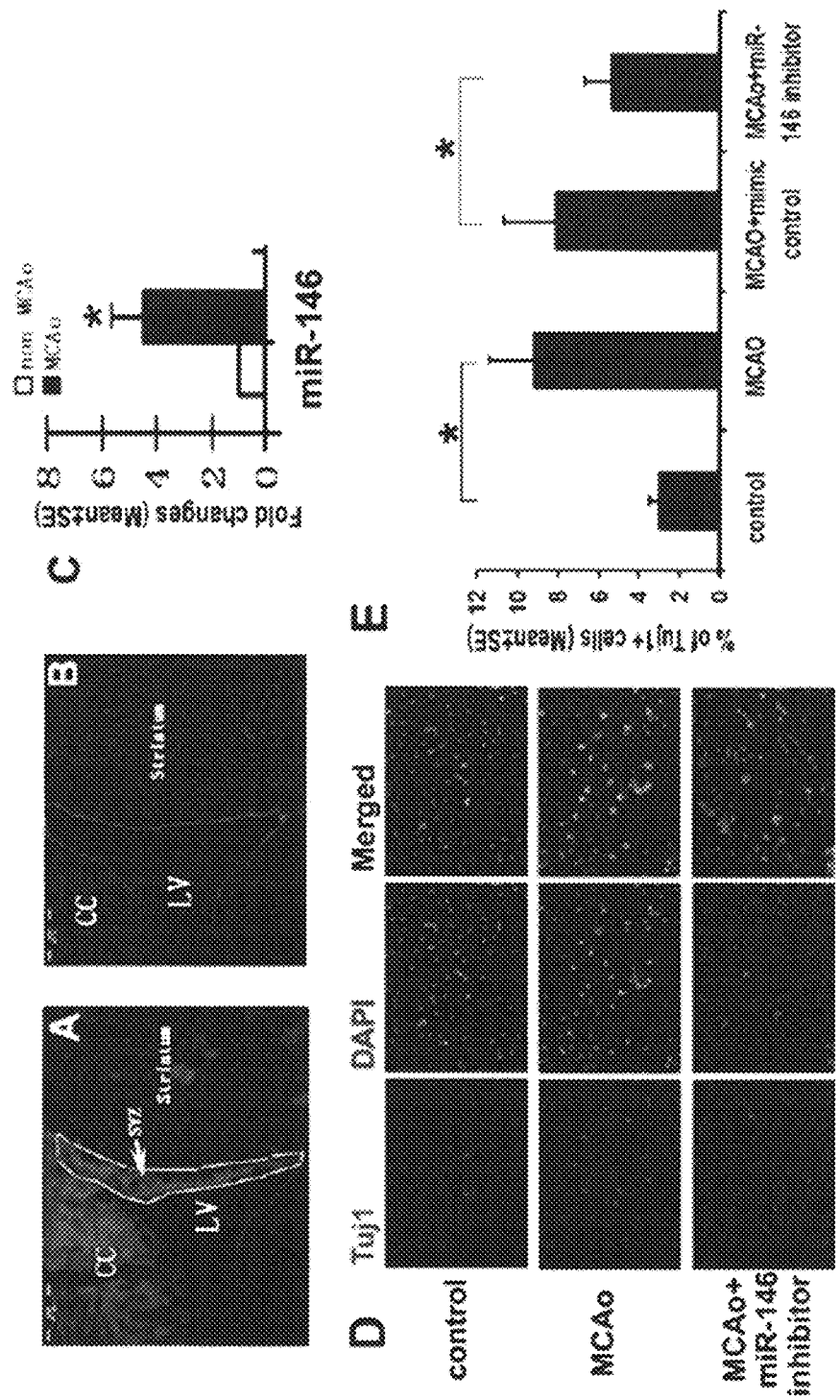
FIG. 3 is comprised of images and data representations showing that stroke upregulates miR-146a in SVZ neural stem cells.

We also examined miR-146a levels post-stroke. FIG. 3 summarizes our results which show that stroke upregulates miR-146a in SVZ neural stem cells. FIGS. 3A and B show SVZ cells before (FIG. 3A) and after (FIG. 3B) laser capture microdissection ("LCM"). Real-time RT-PCR analysis (FIG. 3C) shows miR-146a levels in non-ischemic ("non-MCAO") and ischemic ("MCAO") neural stem cells isolated by LCM. LCM. N=6 rats/group. Immunocytochemistry analysis (FIGS. 3D and E) shows Tuj1 positive neuroblasts in non-ischemic ("non-MCAO") and ischemic ("MCAO") neural stem cells as well as ischemic neural stem cells transfected with miR-146a inhibitor (MCAO+miR-146a inhibitor). N=3/group, *p<0.05.

We first isolated the neural stem cells from the SVZ of adult non-ischemic rats and from rats subjected to middle cerebral artery occlusion ("MCAO") using laser capture microdissection (FIGS. 3A and B). Then, using real-time RT-PCR, we measured miR-146a levels in SVZ neural stem cells and found that stroke substantially increased miR-146a levels (FIG. 3C). When SVZ neural stem cells were cultured in differentiation medium, neural stem cells isolated from ischemic SVZ exhibited considerable increases in neuroblasts measured by Tuj1 positive cells compared to non-ischemic neural stem cells (FIGS. 3D and E). Transfection of miR-146a inhibitor into neural stem cells significantly suppressed ischemia-increased neuroblasts (FIG. 3E), compared with non-ischemic neural stem cells. Our data indicate that miR-146a mediates stroke-induced neurogenesis.

Neurogenesis and oligodendrogenesis are related to neurological function. We also examined whether in vivo elevation of miR-146a improves neurological outcome after stroke. Young adult Wistar rats were subjected to MCAO. Using an Alzet micro-osmotic pump (35 µg, 1 ul/hr, Alzet, Cupertino, Calif., USA), we intraventricularly infused the miR-146a mimic oligonucleotides (e.g., available from Thermo Scientific, Waltham, Mass., USA, or its affiliates as part of the miRIDIAN™ product line) into the ischemic lateral ventricle for 7 days starting 1 day after MCAO (n−4). Ischemic rats (n=7) that received intraventricular infusion of miRNA mimic control (cel-miR-67, 35 µg, Thermo Scientific) were used as a control group. The cel-miR-67 is not expressed in rodent brain. A modified neurological severity score ("mNSS") was performed 1, 3, 7, and 14 days after MCAO by a person who was blinded to the treatment. We found that all rats exhibited severe neurological deficits prior to (1 d after MCAO) the infusion of miR-146a mimics (FIG. 4A). Compared to miRNA control treatment, treatment with miR-146a mimics significantly improved neurological outcome measured by the mNSS starting 7d and persisting to 14 days after stroke (FIG. 4A, p<0.05).

Figure 4:
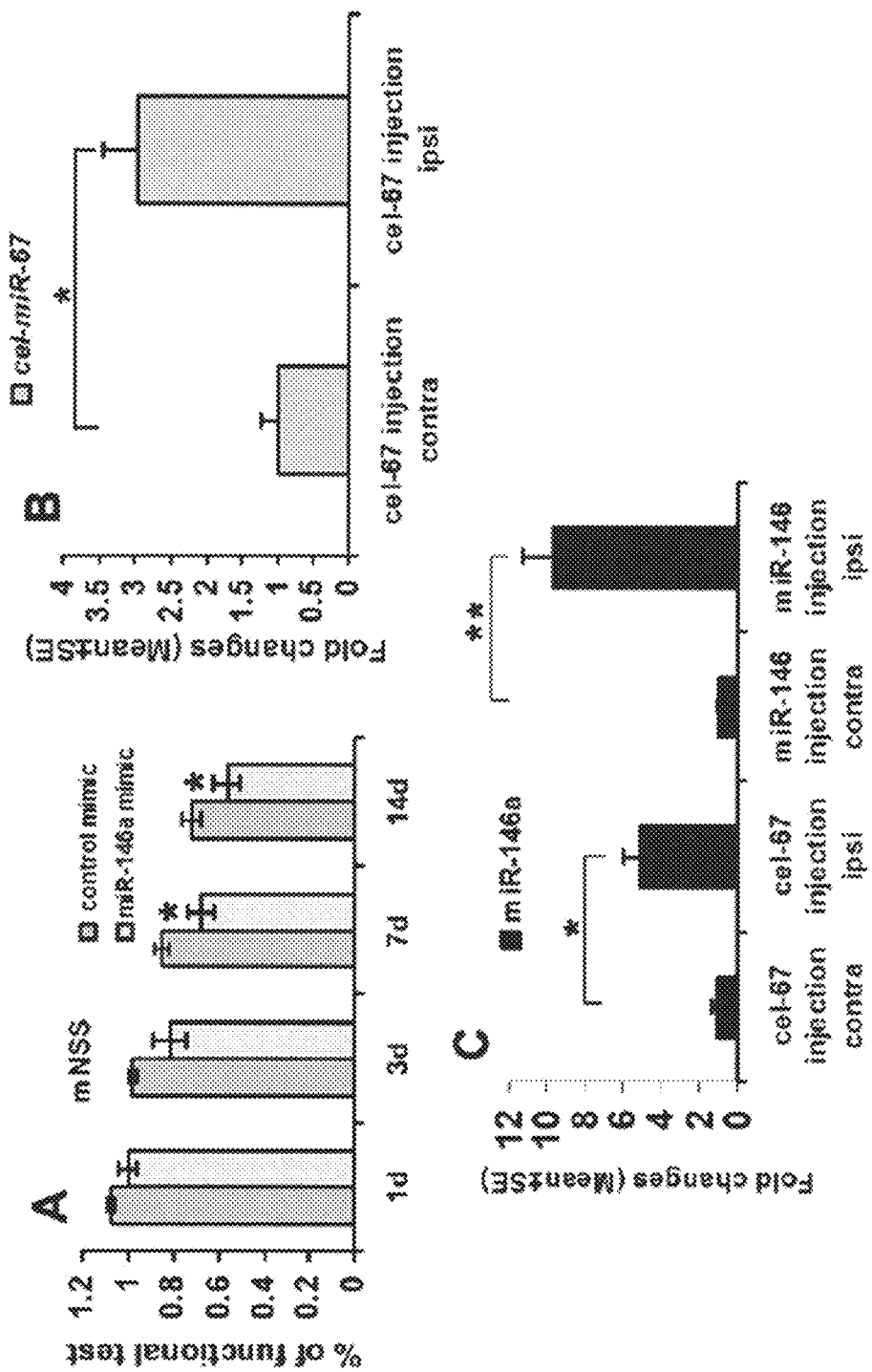
FIG. 4 is comprised of data representations showing the effect of miR-146a treatment on neurological outcome after stroke.

To examine whether intraventricular infusion of miR-146a mimics elevates brain levels of miR-146a, we measured miR-146a and cel-miR-67 levels. FIG. 4 shows the effect of miR-146a treatment on neurological outcome after stroke. FIG. 4A shows that the administration of miR-146a mimics at 24 hours after stroke improved neurological function measured by mNSS 7 and 14 days after MCA occlusion compared with the control mimic treatment group. N=7 rats in control mimic group and N=4 in miR-146 mimic group. FIG. 4B demonstrates that injection of cel-miR-67 mimics substantially increased cel-miR-67 expression in ipsilateral SVZ neural progenitor cells compared with that in contralateral SVZ cells. FIG. 4C shows that the expression of miR-146a was significantly increased after the injection of mimic control—cel-miR-67 and further upregulated after the injection of miR-146a mimics in ipsilateral SVZ. Panels B and C are Taqman real-time RT-PCR data. N=3/group, *p<0.05, **p<0.01.

Briefly, total RNAs were extracted from SVZ tissues of ischemic rats treated with miR-146a or cel-miR-67. Levels of these miRNAs were measured using real-time RT-PCR. We found that intraventricular infusion of cel-miR-67 significantly increased cel-miR-67 levels in the ipsilateral SVZ tissue compared to that in the contralateral SVZ (FIG. 4B), while miR-146a levels in the ipsilateral SVZ were 5.1 fold compared to the contralateral SVZ (FIG. 4C). This elevated miR-146a level in the ipsilateral SVZ after infusion of cel-miR-67 is comparable to the level observed in the ischemic SVZ of rats without the cel-miR-67 treatment (FIG. 2C). Thus, the increased miR-146a detected after infusion of cel-miR-67 is likely induced by ischemia but not by cel-miR-67. However, intraventricular infusion of miR-146a mimics increased miR-146a levels of the ipsilateral SVZ from 1.0 to 9.7 fold compared to the levels in the contralateral SVZ (FIG. 4C). We did not detect cel-miR67 signals (Ct values above 40) in rats treated with miR-146a. These findings indicate that the intraventricular infusion of miR-146a mimics specifically elevate brain miR-146a levels.

Collectively, these data indicate that elevation of brain miR-146a levels by exogenous miR-146a mimics considerably improves neurological outcomes after stroke.

Diabetes induces downregulation of miR-146a in dorsal root ganglion ("DRG") neurons and peripheral neuropathy. Elevation of miR-146a by phosphodiesterase 5 inhibitors, as a nonlimiting example, sildenafil, improves neurological outcomes in diabetic peripheral neuropathy.

Figure 5:
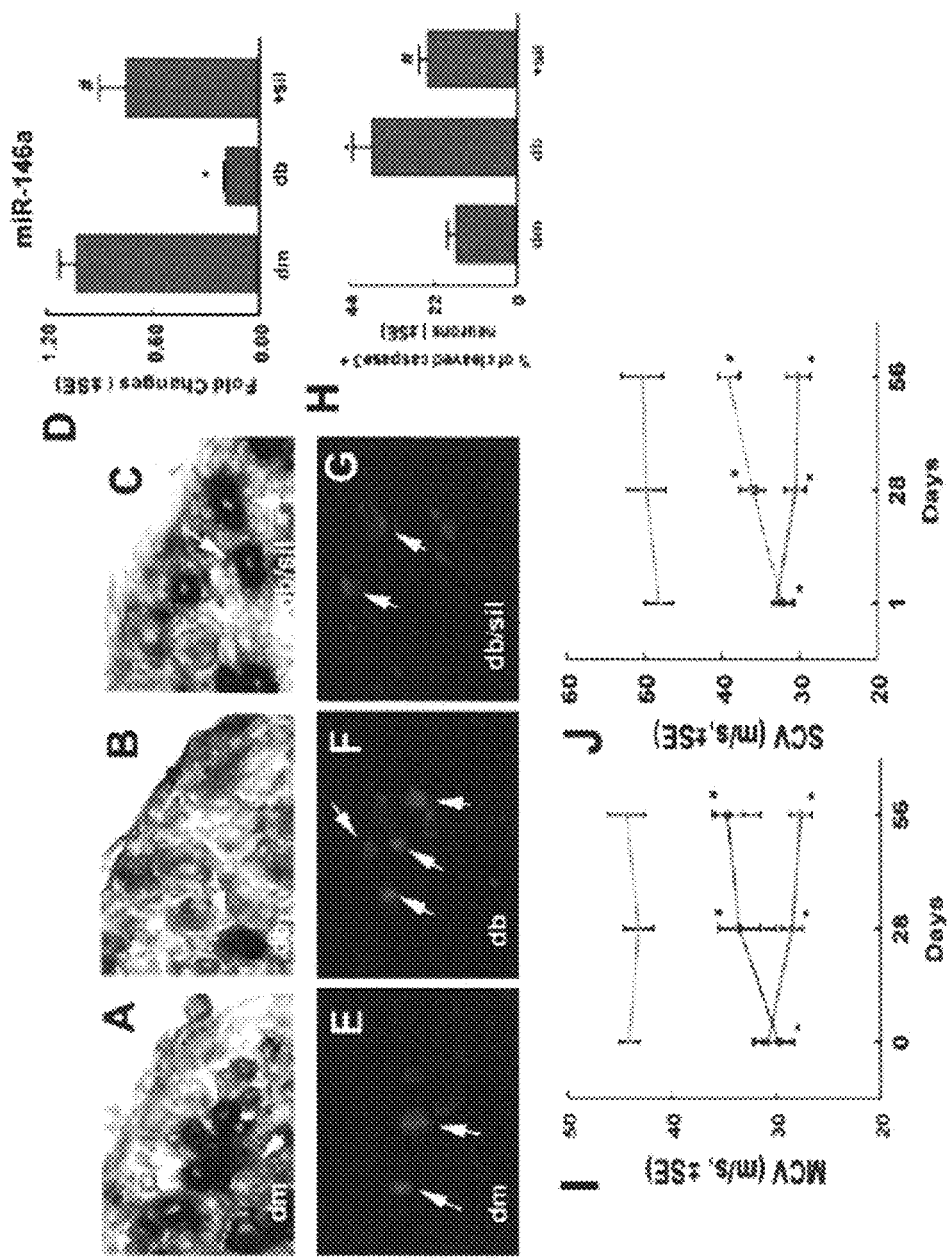
FIG. 5 is comprised of images and data representations showing the effects of expression of miR-146a and caspase 3 and neurological function in diabetic mice (db/db mice).

DRG neurons play an important role in sensory conduction. Diabetic peripheral neuropathy is characterized by the loss and/or degeneration of neurons and the slowing of nerve conduction velocities. Using a mouse model of type II diabetes which develops severe peripheral neuropathy, we measured miR-146a expression in DRG neurons. In situ hybridization and real-time RT-PCR analyses revealed that miR-146a signals were substantially reduced in DRG neurons of type II diabetic mice compared that in non-diabetic mice (FIG. 5). FIG. 5 shows expression of miR-146a and caspase 3 and neurological function in diabetic mice (db/db mice). In situ hybridization (FIG. 5A to C) shows miR146a signals (arrows) in representative DRG neurons of non-diabetic mouse (FIG. 5A, dm), diabetic mouse (FIG. 5B, db/db) and diabetic mouse treated with sildenafil (FIG. 5C, db/sil). FIG. 5D shows quantitative data of miR-146a levels in these three population mice measured by real-time RT-PCR. Immunofluorescent staining (FIG. 5E to G) shows caspase 3 positive DRG neurons in non-diabetic (FIG. 5E, dm), diabetic (FIG. 5F, db) and diabetic mice treated with sildenafil (FIG. 5G, db/sil). FIG. 5H is quantitative data of caspase 3 positive cells. FIGS. 5I and J are neurological function measured by motor nerve conduction velocity (MCV, FIG. 5I) and sensory nerve conduction velocity ("SCV", FIG. 5J). Red, blue, and black lines represent non-diabetic mice, diabetic mice treated with saline, and diabetic mice treated with sildenafil, respectively. *P<0.01 versus the nondiabetic group. #P<0.05 versus the diabetic group treated with saline. n=10/group. DRG neurons with reduction of miR-146a exhibited apoptosis measured by cleaved caspase 3 immunoreactive cells (FIG. 5). Elevation of miR-146a in DRG neurons by sildenafil rescued diabetes-induced DRG neuron death and improved neurological outcomes (FIG. 5).

Figure 6:
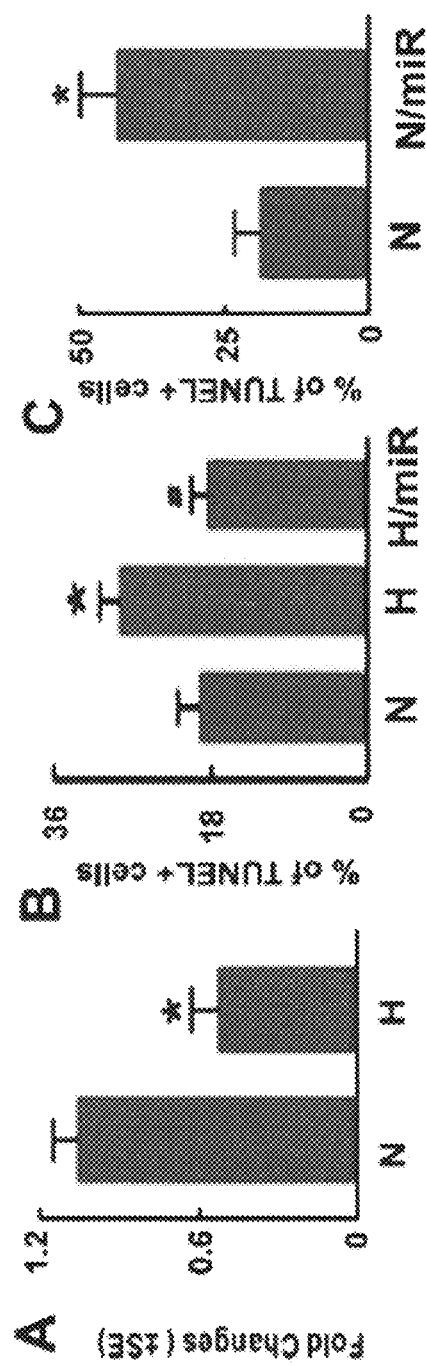
FIG. 6 is comprised of data representations showing the effect of miR-146a on cultured DRG neurons.

In vitro, hyperglycemia significantly suppressed miR-146a expression in cultured primary DRG neurons, which was associated with DRG neuron death (FIG. 6). FIG. 6 shows the effect of miR-146a on cultured DRG neurons. FIG. 6A is real-time RT-PCR data showing miR-146a levels in DRG neurons cultured under normal glucose (N) and high glucose (H) conditions. Substantial reduction of miR-146a was detected under high glucose condition (n=6, *p<0.05). FIG. 6B shows percentage of TUNEL positive DRG neurons under normal glucose (N), high glucose (H), and high glucose with miR-146a mimics (H/miR). * and # p<0.05 vs. normal and high glucose, respectively, n=6/group. FIG. 6C shows percentage of TUNEL positive DRG neurons under normal glucose (N) and normal glucose with siRNA against miR-146a (N/siR). Attenuation of endogenous miR-146a with siRNA against miR-146a significantly (p<0.05, n=6/group) increased TUNEL positive cells. Treatment of DRG neurons with miR-146a mimics completely abolished hyperglycemia-induced reduction of miR-146a and neuronal death (FIG. 6). In addition, attenuation of endogenous miR-146a in DRG neurons by siRNA against miR-146a resulted in considerable increases in neuronal death measured by TUNEL positive cells (FIG. 6).

Collectively, our in vivo and in vitro data indicate that downregulation of miR-146a in DRG neurons by diabetes induces neuronal death, whereas elevation of miR-146a levels suppresses diabetes-induced DRG neuron death, leading to improvement of neurological outcomes. Our data indicates that elevation of miR-146a levels in the ischemic brain significantly improves neurological outcomes after stroke and that, without limitation to any specific mechanism, enhancement of neurogenesis and oligodendrogenesis by miR-146a is likely a mechanism underlying the improved neurological outcome. Moreover, elevation of miR-146a in DRG neurons in diabetic peripheral neuropathy substantially reduces DRG neuron death and improves neurological function. Thus, in accordance with some embodiments, miR-146a is a therapeutic target for treatment of neurological conditions, disease, or injury, including but not limited to, stroke, brain injury, neurodegenerative diseases, and peripheral neuropathy.

Some embodiments comprise miR-146a as a therapeutic target to enhance neurogenesis and oligodendrogenesis in adult neural stem cells and OPCs, which facilitates repair processes in injured brain and in neurodegenerative diseases. In addition, this therapeutic target reduces diabetes-induced DRG neuron death and improves neurological function in diabetic peripheral neuropathy.

In some embodiments, without limitation, miR-146a increases neuronal differentiation of neural progenitor cells, promotes maturation of OPCs, and improves neurological outcome post stroke. The results, which were obtained in a widely accepted neural stem cell assay, were validated in an animal model of stroke. New neurons enhance neuronal function including memory, while mature oligodendrocytes myelinate axons. Furthermore, miR-146a reduces diabetes-induced DRG neuron death and improves neurological outcomes in diabetic peripheral neuropathy. Thus, in accordance with some embodiments, miR-146a can be used as a treatment or target for therapeutic approaches against neurological conditions, disease, or injury, as nonlimiting examples, brain injuries, such as stroke and traumatic brain injury, neurodegenerative diseases, such as multiple sclerosis and dementia and peripheral neuropathies, including but not limited to, diabetic peripheral neuropathy.

Example 2

In our work, we evaluated whether thymosin beta 4 ("Tβ4") promotes differentiation of oligoprogenitor cells to oligodendrocytes in animal models of neurological injury. We discovered unexpectedly that Tβ4 increased expression of microRNA-146a and suppressed expression of proinflammatory cytokines of the Toll-like receptor ("TLR") signaling pathway, and that Tβ4 suppresses the TLR proinflammatory pathway by upregulating miR146a, with implication for the promotion of oligodendrogenesis for clinical purposes.

Tissue inflammation results from neurological injury and regulation of the inflammatory response is vital for neurological recovery. The innate immune response system which includes the Toll-like receptor ("TLR") proinflammatory signaling pathway regulates tissue injury. We evaluated whether that Tβ4 regulates the TLR proinflammatory signaling pathway. Since oligodendrogenesis plays an important role in neurological recovery, we employed an in vitro primary rat embryonic cell model of oligodendrocyte progenitor cells ("OPCs") and a mouse N20.1 OPC cell line to measure the effects of Tβ4 on the TLR pathway. In brief summary, we grew cells in the presence of Tβ4 ranging from 25 to 100 ng/ml of (RegeneRx Biopharmaceuticals Inc., Rockville, Md.) for 4 days.

Quantitative real-time ("Qrt:") PCR and Western blot data demonstrated that Tβ4 treatment increased expression of microRNA-146a (also "miR-146a"), a negative regulator of the TLR signaling pathway, in these two cell models. Western blot analysis showed that Tβ4 treatment suppressed expression of IL-1 receptor associated kinase 1 ("IRAK1") and TNF receptor-associated factor 6 ("TRAF6"), two proinflammatory cytokines of the TLR signaling pathway. Transfection of miR-146a into both primary rat embryonic OPCs and mouse N20.1 OPCs treated with Tβ4 demonstrated an amplification of myelin basic protein ("MBP") expression and differentiation of OPCs into mature MBP expressing oligodendrocytes. Transfection of anti-miLR-146a nucleotides reversed the inhibitory effect of Tβ4 on IRAK1 and TRAF6 and decreased expression of MBP. Our data indicate that Tβ4 promotes OPC differentiation at least in part by suppressing the TLR proinflammatory pathway via upregulating miR146a.

Tβ4 is a 5K Dalton, 43-amino acid peptide originally isolated from the thymus gland (SEQ ID NO: 2, Ac-Ser-Asp-Lys-Pro-Asp-Met-Ala-Glu-Ile-Glu-Lys-Phe-Asp-Lys-Ser-Lys-Leu-Lys-Lys-Thr-Glu-Thr-Gln-Glu-Lys-Asn-Pro-Leu-Pro-Ser-Lys-Glu-Thr-Ile-Glu-Gln-Glu-Lys-Gln-Ala-Gly-Glu-Ser). Improvement in neurological outcome is associated with oligodendrogenesis, i.e., differentiation of oligoprogenitor cells ("OPC") into mature myelin secreting oligodendrocytes ("OL"). Oligodendrogenesis contributes to remyelination after neurological injury by differentiation of OPCs into mature myelin expressing OL.

The innate immune system has been implicated in mediating the inflammatory response to cardiac injury and disease. Toll-like receptors ("TLRs") are pattern recognition receptors that recognize conserved molecular patterns of pathogens. In addition to pathogens, TLRs also recognize damage-associated molecular patterns ("DAMPs") which are molecular patterns of endogenous host debris released during cellular injury or death. This debris can be extracellular matrix protein, oxidized proteins, RNA or DNA. Once recognition occurs, the TLRs are stimulated resulting in activation of many signaling pathways, including those pathways involving the mitogen activated protein kinases ("MAPKs") and the nuclear factor NF-κB transcription factors. The MAPKs activate OL differentiation, and therefore TLR signaling may be involved in oligodendrogenesis as well as in regulating the inflammatory response. In addition, the TLR pathways are affected by miR-146, which downregulates proinflammatory cytokine production and activation of inflammatory pathways. TLR4 is a well-studied TLR which mediates its proinflammatory response through three proteins, IRAK1 (IL-1 receptor-associated kinase 1), IRAK4 and TRAF6 (tumor necrosis receptor associated factor 6). By targeting IRAK1 and TRAF6, miR-146 inhibits NF-κB activation. We evaluated whether Tβ4 inhibits the TLR proinflammatory signaling pathway by specifically increasing miR-146a to promote differentiation of OPCs to MBP expressing OLs.

Experimental Procedures

All animal experiments were performed according to protocols approved by the Henry Ford Hospital Institutional Animal Care and Use Committee.

Isolation of Primary Rat Embryonic OPCs

Primary rat embryonic OPCs were isolated and prepared according to the method known to the skilled artisan. Briefly, on embryonic day 17, rat embryos were removed from a pregnant Wistar rat in a laminar flow hood. The cortices were dissected out by using microdissecting scissors, rinsed twice in Hank's buffered salt solution and dissociated after digesting with 0.01% trypsin and DNase at 37° C. for 15 min. The digested cells were washed twice, filtered through a 70 mm nylon cell strainer and plated with DMEM containing 20% fetal bovine serum (FBS) in poly-D-lysine coated T75 cell culture flasks (approximately 10 million cells per flask). The cells grew to confluence for 10 days and then were placed on the shaker at 200 r.p.m. at 37° C. for 1 h to remove microglial cells. Subsequently, the cells were left on the shaker for an additional 18-20 h to collect OPCs. The collected OPCs were plated in untreated Petri dishes for 1 h to remove contaminated microglia and astrocytes which attach to the Petri dish more efficiently than OPCs. The unattached OPCs were transferred onto poly-D, L-ornithine-coated Petri dishes at a cell density of $10^4$ per/cm2 with a basal chemically defined medium ("BDM") containing 10 ng/ml platelet-derived growth factor-alpha ("PDGF-AA") and 10 ng/ml basic fibroblast growth factor ("bFGF") for 7-10 days.

Cell Culture, Transfection and Treatment with Tβ4

The mouse primary cultures of OPCs were conditionally immortalized by transformation with a temperature-sensitive large T-antigen into a mouse OPC cell line-N20.1 (21). N20.1 cells were provided by Dr. Anthony Campagnoni (University of California at Los Angeles). N20.1 cells were grown and maintained in Dulbecco's modified Eagle's medium ("DMEM")/F12 with 1% fetal bovine serum ("FBS") and G418 (100 µg/ml) at 37° C. For N20.1 cells, transient transfections were performed with Nucleofector kit according to the manufacturer's protocol (Amaxa, Germany). The cells ($10^6$) were mixed with 1 µg plasmid DNA or 100 pmol of siRNA/oligo nucleotides and pulsed according to the manufacturer's instruction. The transfected cells were immediately plated into Petri dishes with DMEM containing 1% FBS and incubated at 37° C. for days. Primary rat embryonic OPCs were transiently transfected with Lipofectamine (Invitrogen) overnight, according to the manufacturer's protocol (see Chew et al., J. Neuroscience 30(33): 11011-11027 (2010)). Amounts of DNA and siRNA/oligo nucleotides were used as recommended by the manufacturer. The control plasmid (pcDNA3) was used as a mock transfected control for miR-146a expression vector transfection, and control siRNA (Ambion, a random mixture of oligonucleotides) was used as a mock transfected control for both transfections with Tβ4siRNA and anti-miR-146a inhibitor nucleotides. The cells ($10^4$ cells/cm$^2$) were treated with 0, 25, 50, 100 ng/ml of Tβ4 (RegeneRx Biopharmaceuticals Inc., Rockville, Md.). The cells were incubated at 37° C. and fed every 2 days with fresh medium (DMEM containing 1% FBS for N20.1 cells and BDM for primary rat embryonic OPCs) with and without Tβ4 for 4 days. To test for LPS contamination in Tβ4, the cells were cultured in the presence of the LPS inhibitor polymyxin B (50 µg/ml) followed by treatment with Tβ4. Tβ4 (100 ng/ml) was boiled for 10 minutes in order to denature Tβ4 protein and was used as a negative control. Transfected cells ($2\times10^4$ cells/cm2) including mock transfected controls were treated with and without 100 ng/ml of Tβ4 (RegeneRx Biopharmaceuticals Inc., Rockville, Md.) for 4 days and fresh medium was provided at day 2 with/without Tβ4.

Quantitative Real Time PCR ("qrtPCR")

The extraction of total RNA and preparation of cDNA were performed as known to the skilled artisan. The QrtPCR amplification was done for 40 cycles in the following thermal cycle: 95° C. for 30 s, 60° C. for 30 s, and 72° C. for 45 s using SYBR green (Life Technologies, Grand Island, N.Y.). The primer sequences were:

```
CNPase:
Forward-
                                  (SEQ ID NO: 3)
5T-TACTTCGGCTGGTTCCTGAC-3T 5T-

Reverse-
                                  (SEQ ID NO: 4)
T-GCCTTCCCGTAGTCACAAAA-3T 5T-

(m,r) MBP:
Forward-
                                  (SEQ ID NO: 5)
ATGGCATCACAGAAGAGACCCTCA-3' 5T-

Reverse-
                                  (SEQ ID NO: 6)
TAAAGAAGCGCCCGATGGAGTCAA-3' 5'-

(m,r) p38 (r):
Forward-
                                  (SEQ ID NO: 7)
ATGACGAAATGACCGGCTAC-3' 5T-

Reverse-
                                  (SEQ ID NO: 8)
ACAACGTTCTTCCGGTCAAC-31 5T- p38 (m):
Forward-
                                  (SEQ ID NO: 9)
GCTGAACAAAGGGAGAGACG-3T 5T-

Reverse-
                                  (SEQ ID NO: 10)
TGCTTTCTCCCCAAATTGAC-3T 5T-

JNK1 (r):
Forward-
                                  (SEQ ID NO: 11)
TTCAATGTCCACAGATCCGA-3T 5'-

Reverse-
                                  (SEQ ID NO: 12)
CTAACCAATTCCCCATCCCT-3T 5T-

JNK1 (m):
Forward-
                                  (SEQ ID NO: 13)
GCCATTCTGGTAGAGGAAGTTTCTC-3' 5T-

Reverse-
                                  (SEQ ID NO: 14)
CGCCAGTCCAAAATCAAGAATC-3' 5T-

Jun (r):
Forward-
                                  (SEQ ID NO: 15)
TGAAGCAGAGCATGACCTTG-3' 5T-

Reverse-
                                  (SEQ ID NO: 16)
CACAAGAACTGAGTGGGGGT-3' 5T-

Jun (m):
Forward-
                                  (SEQ ID NO: 17)
CGCAACCAGTCAAGTTCTCA-3T Reverse-
                                  (SEQ ID NO: 18)
GAAAAGTAGCCCCCAACCTC-3T.
```

After qrtPCR, agarose gel electrophoresis was performed to verify the quality of the qrtPCR products. No secondary products were detected. Each sample was tested in triplicate and all values were normalized to GAPDH. Values obtained from three independent experiments were analyzed relative to gene expression data using the $2^{-\Delta\Delta CT}$ method.

Quantification of Mature miRNAs by Real-Time qrtPCR

The cDNA for each miR and TaqMan assay were performed in triplicate according to the manufacturer's protocol specified in Applied Biosystems ViiA™ 7 Real-Time PCR System (Applied Biosystem). Briefly, total RNA was isolated with TRIzol (Qiagen). Reverse transcription reaction mixture contained 1-10 ng total RNA, 5 U MultiScribe Reverse Transcriptase, 0.5 mM each dNTPs, 1× Reverse Transcription buffer, 4 U RNase Inhibitor, and nuclease free water. The microRNA cDNA was performed by individual reverse transcription in the following thermal cycle 16° C. for 30 min, 42° C. for 30 min, 85° C. for 5 mM, and then hold at 4° C. for TaqMan assays. TaqMan assay was performed in 20 µl TaqMan real-time PCR reactions containing 1×TaqMan Universal PCR Master Mix No AmpErase UNG, 1×TaqMan miRNA assay, 1.330 of undiluted cDNA, and nuclease free water. All values were normalized to U6 snRNA TaqMan miRNA control assay (Applied Biosystem) as the endogenous control. Values obtained from three independent experiments were analyzed relative to gene expression data using the $2^{-\Delta\Delta CT}$ method.

Western Blot Analysis

Total protein extracts from the cells were prepared, as known to the skilled artisan. The protein extracts were separated by sodium dodecyl sulfate-polyacrylamide gel electrophoresis for Western blot analysis. For Western blot analysis, rabbit antiserum for MBP (1:200; Dako, Carpinteria, Calif.), monoclonal antibodies (1:1000) for p38MAPK, phosphorylated p38MAPK, c-JUN, phosphorylated c-JUN (1:1000; Upstate, Charlottesville, Va., USA), rabbit polyclonal antibodies (1:1000) for JNK1 and phosphorylated JNK1 (Promega Corporation), goat polyclonal TLR2, rabbit polyclonal TLR4, mouse monoclonal IRAK1 antibodies (1:1000), rabbit polyclonal TRAF6 antibodies (1:1000) mouse monoclonal β-actin antibodies (1:5000; Santa Cruz Biotechnology) and mouse monoclonal α-tubulin antibodies (1:5000; Sigma) were used. Donkey anti-goat, anti-rabbit, and anti-mouse horseradish peroxidase (1:5000; Jackson ImmunoResearch Labs, West Grove, Pa., USA)

were used as secondary antibodies. Each experiment was repeated at least three times. The protein bands were quantified based on histogram analysis relative to gel loading marker α-tubulin.

Immunochemistry

Immunofluorescence staining was performed in N20.1 and primary rat embryonic OPC cells. These cells were fixed with 4% paraformaldehyde for 1 h, washed with PBS, blocked with 1% serum for 1 h and incubated with monoclonal antibodies of OPC marker—O4, (1:1000, Chemicon, Billerica, Mass., USA) and a polyclonal antibody against mature OL marker—MBP (1:200; Dako, Carpinteria, Calif.) at room temperature for one hour, rinsed with PBS and secondary antibodies labeled with cyanine fluorophore (Cy3—red fluorescence) for 1 h. The slides were counterstained with 4',6-diamidino-2-phenylindole (DAPI—blue fluorescence) and examined under Fluorescent Illumination Microscope (Olympus IX71/IX51, Tokyo, Japan). DAPI positive cells were considered as total number of cells.

Statistical Analysis

Figure 7:
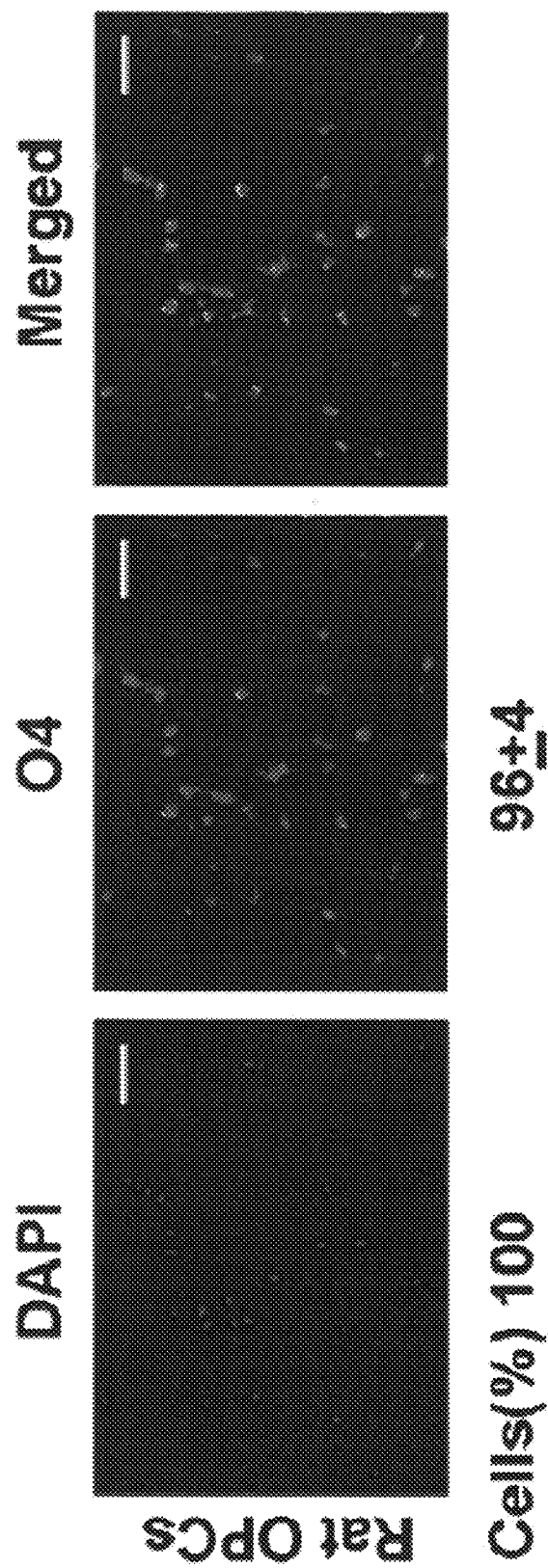
FIG. 7 is comprised of images showing immunostaining of primary rat embryonic OPCs.
Figure 8:
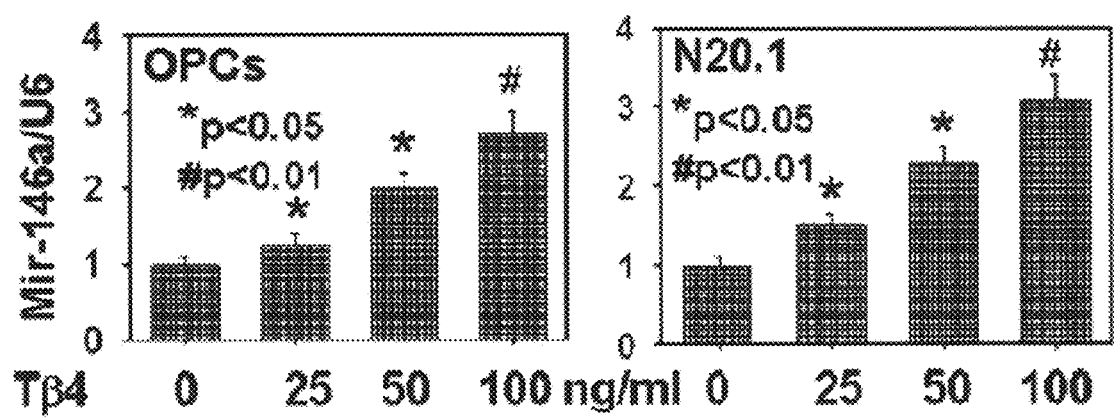
FIG. 8 is comprised of data representations showing microRNA analysis of miR-146a in OPCs after Tβ4 treatment by qrtPCR.

Data were summarized using mean and standard deviation. To compare the differences between cell cultures with and without Tβ4 treatment, a one sample t-test or a two-sample t-test was used. For the comparisons of QrtPCR of mRNA/GAPDH and Quantitative Real Time PCR ("qrt-PCR") of miR-146a/U6, controls were normalized to 1, so that one-sample t-test was used for analysis. To compare the percentage of positive stained cells out of the total number of cells between Tβ4 treatment and control, a two-sample t-test was used. P-value<0.05 was considered significant Results We discovered unexpectedly that Tβ4 increases expression of miR-146a in OPCs. We investigated the effect of Tβ4 treatment on the expression of miR-146a and miR-146a in primary rat embryonic OPCs (n=5) and in a mouse OPC cell line—N20.1 (n=5) by qrtPCR. Purity of rat primary OPCs used in the experiments was confirmed by immunostaining for O4 and was quantified by cell counting. The cell counting data showed that >90% of these cells were O4 positive. FIG. 7 shows immunostaining of primary rat embryonic OPCs. Primary rat embryonic OPCs were immunostained for O4 labeled with fluorescence Cy3 and counter stained for nuclei with DAPI. The cells were quantified by counting as percentage of O4 positive cells when DAPI positive cells were considered as total number of cells (shown at the bottom). We found that Tβ4 treatment induced the expression of miR-146a in rat primary embryonic OPCs and mouse N20.1 cells in a dose-dependent manner (FIG. 8). In contrast, Tβ4 treatment had no effect on miR-146a expression in rat primary embryonic OPCs and mouse N20.1 cells (data not shown). FIG. 8 shows microRNA analysis of miR-146a in OPCs after Tβ4 treatment by qrtPCR. The total RNA samples were extracted from primary rat embryonic OPCs (left panel) and mouse OPC cell line—N20.1 (right panel) after the treatment with Tβ4 at the dose ranging from 0 to 100 ng/ml (shown at the bottom) for microRNA analysis of miR-146a by qrtPCR. Note that expression miR-146a was increased in a dose dependent manner in both OPCs. P<0.05 was considered as significant. We also discovered unexpectedly that Tβ4 down regulates the intracellular TLR signaling pathway in OPCs. MiR-146a targets two proinflammatory cytokines, IRAK1 and TRAF6, in the intracellular TLR signaling pathway. We evaluated the effect of Tβ4 treatment on the TLR signaling pathway in rat primary embryonic OPCs and mouse N20.1 cells. These cell cultures which demonstrated induction of miR-146a expression after Tβ4 treatment (FIG. 8) were utilized to analyze the expression levels of IRAK1, TRAF6 and MBP, the mature OL marker, by Western blot. Tβ4 treatment markedly reduced the expression levels of IRAK1 and TRAF6, and increased the expression level of MBP in a dose-dependent manner in rat primary embryonic OPCs (n=3) and mouse N20.1 OPCs (n=3) (FIG. 9).

Figure 9:
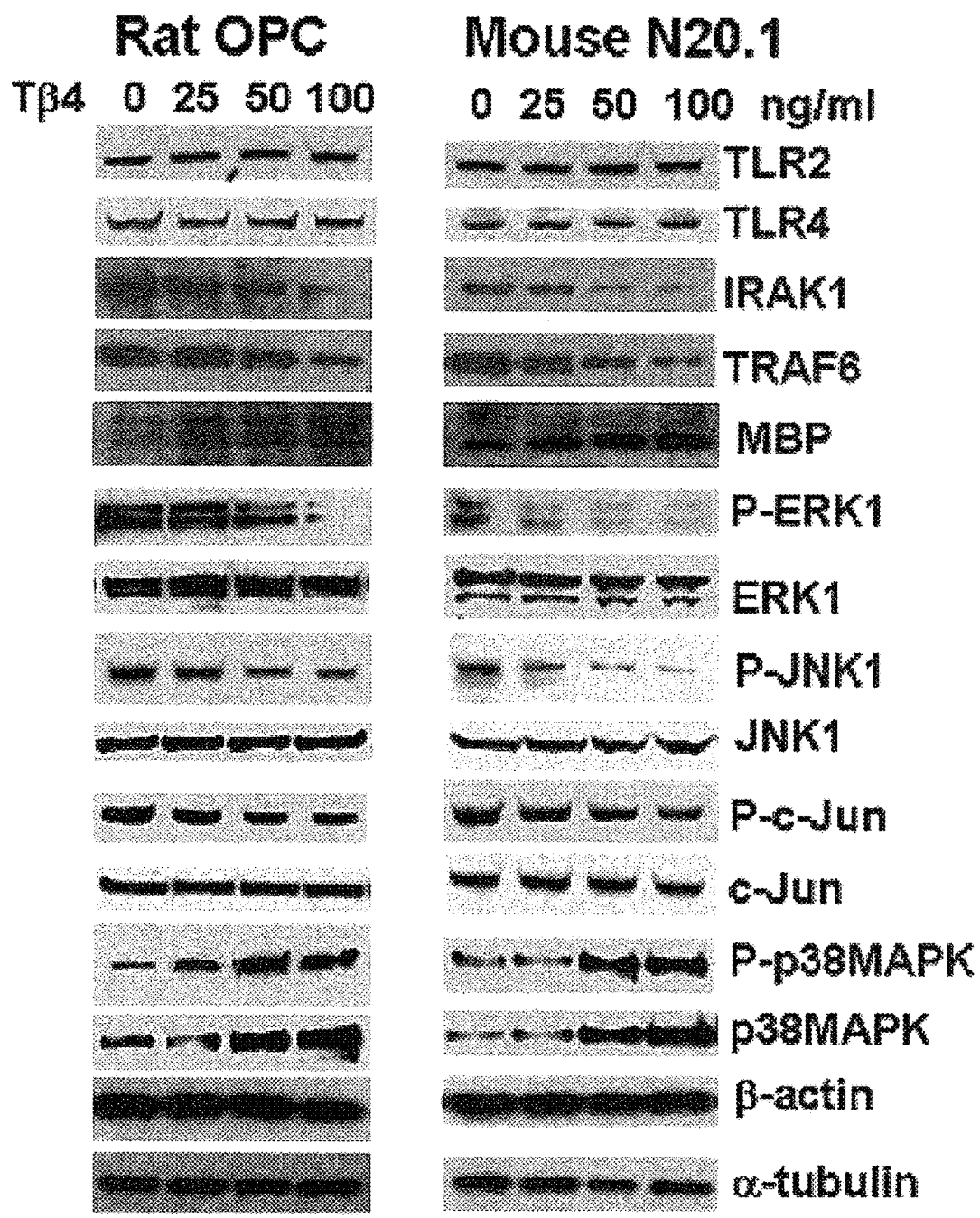
FIG. 9 is comprised of images showing Western blot analysis of downstream signaling mediators of TLR in OPCs after Tβ4 treatment.

FIG. 9 shows Western blot analysis of downstream signaling mediators of TLR in OPCs after Tβ4 treatment. The protein samples were separated, transferred and analyzed from the primary rat embryonic OPCs (left panel) and mouse OPC cell line-N20.1 (right panel) after the treatment with Tβ4 at the dose ranging from 0 to 100 ng/ml (shown at the top) and analyzed for different protein expressions. Migrations of proteins are shown at right. The loading of the samples were normalized with β-actin and α-tubulin. These data indicate that the TLR signaling pathway may be involved in Tβ4 mediated OL differentiation in primary rat embryonic OPCs and mouse N20.1 cells.

Figure 10:
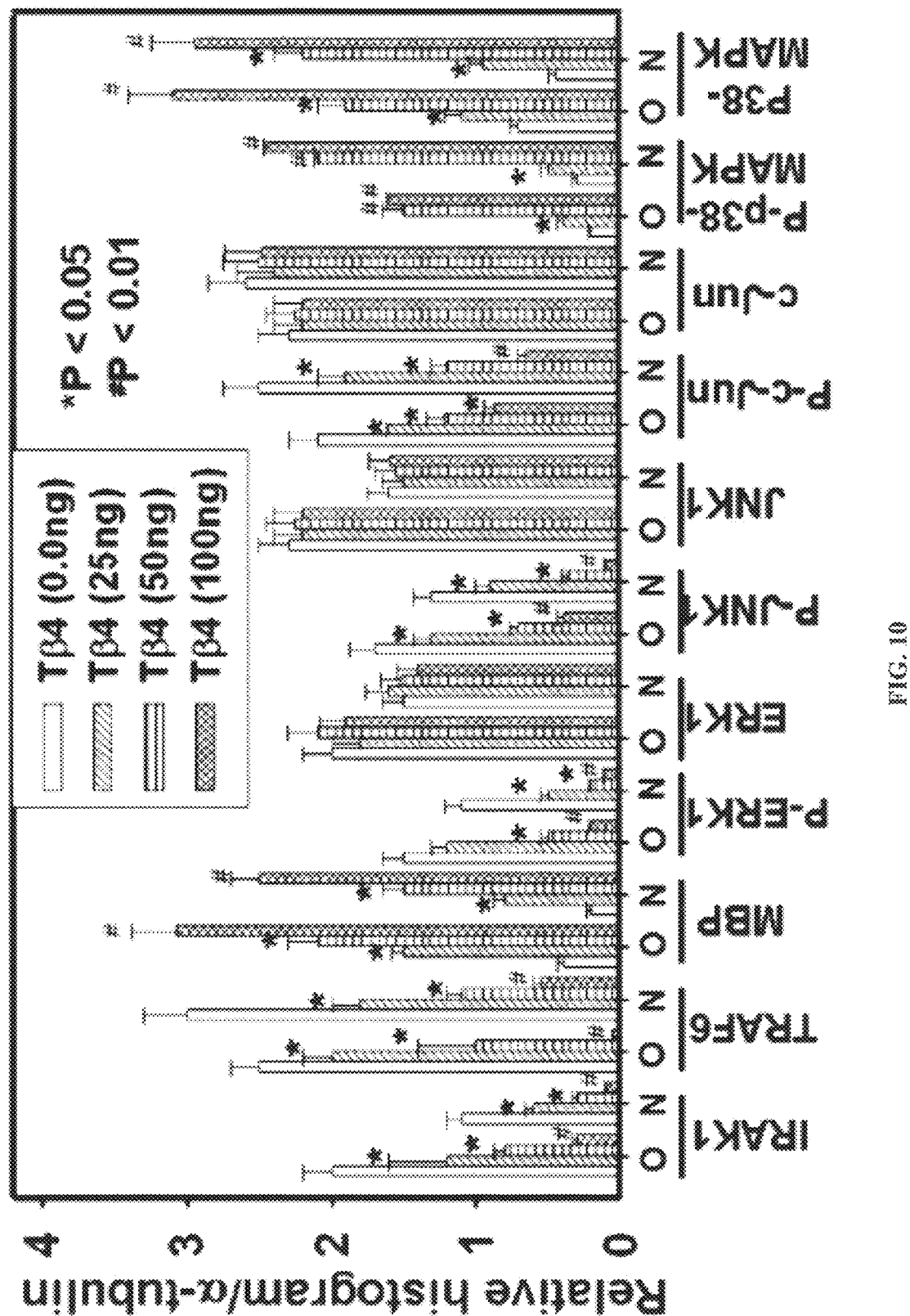
FIG. 10 is comprised of data representations showing quantitative analysis of expression of IL-1 receptor-associated kinase 1 ("IRAK1"), tumor necrosis receptor associated factor 6 ("TRAF6"), myelin basic protein ("MBP"), phosphorylated ERK1 ("P-ERK1"), ERK1, phosphorylated JNK1 ("P-JNK1"), JNK1, phosphorylated c-JUN ("P-c-JUN"), c-JUN, phosphorylated p38MAPK "(P-p38MAPK") and p38MAPK at the protein level after Tβ4 treatment.

FIG. 10 shows quantitative analysis of expression of IRAK1, TRAF6, MBP, phosphorylated ERK1 (P-ERK1), ERK1, phosphorylated JNK1 (P-JNK1), JNK1, phosphorylated c-JUN (P-c-JUN), c-JUN, phosphorylated p38MAPK (P-p38MAPK) and p38MAPK at the protein level after Tβ4 treatment. Western blot data from the primary rat embryonic OPCs (O) and mouse OPC cell line—N20.1 (N) after treatment with Tβ4 at the dose ranging 0, 25, 50 and 100 ng/ml were quantified based on histogram analysis in compared to α-tubulin. The bar graph indicates relative protein expression in compared to α-tubulin. P<0.05 was considered as significant.

We discovered unexpectedly that downstream signaling of the MAPKs in Tβ4 mediates oligodendrocyte differentiation. We evaluated the effect of Tβ4 on MAPKs which are downstream of the TLR pathway. Expression of TLR2 and TLR4 were confirmed by Western blot analysis (FIG. 9). However, treatment with Tβ4 had no effect on expression of TLR2 and TLR4 (FIG. 9, FIG. 10). Western blot was performed to measure expression and phosphorylation of p38MAPK, ERK1, JNK1, and c-Jun after Tβ4 treatment (FIG. 9, FIG. 10). Tβ4 treatment induced expression and phosphorylation of p38MAPK, a known regulator of oligodendrocyte differentiation, in a dose-dependent manner. In contrast, Tβ4 dose-dependently inhibited the phosphorylation of ERK1/2, JNK1 and c-Jun in primary rat embryonic OPCs and mouse N20.1 cells (FIG. 9, FIG. 10).

Figure 11:
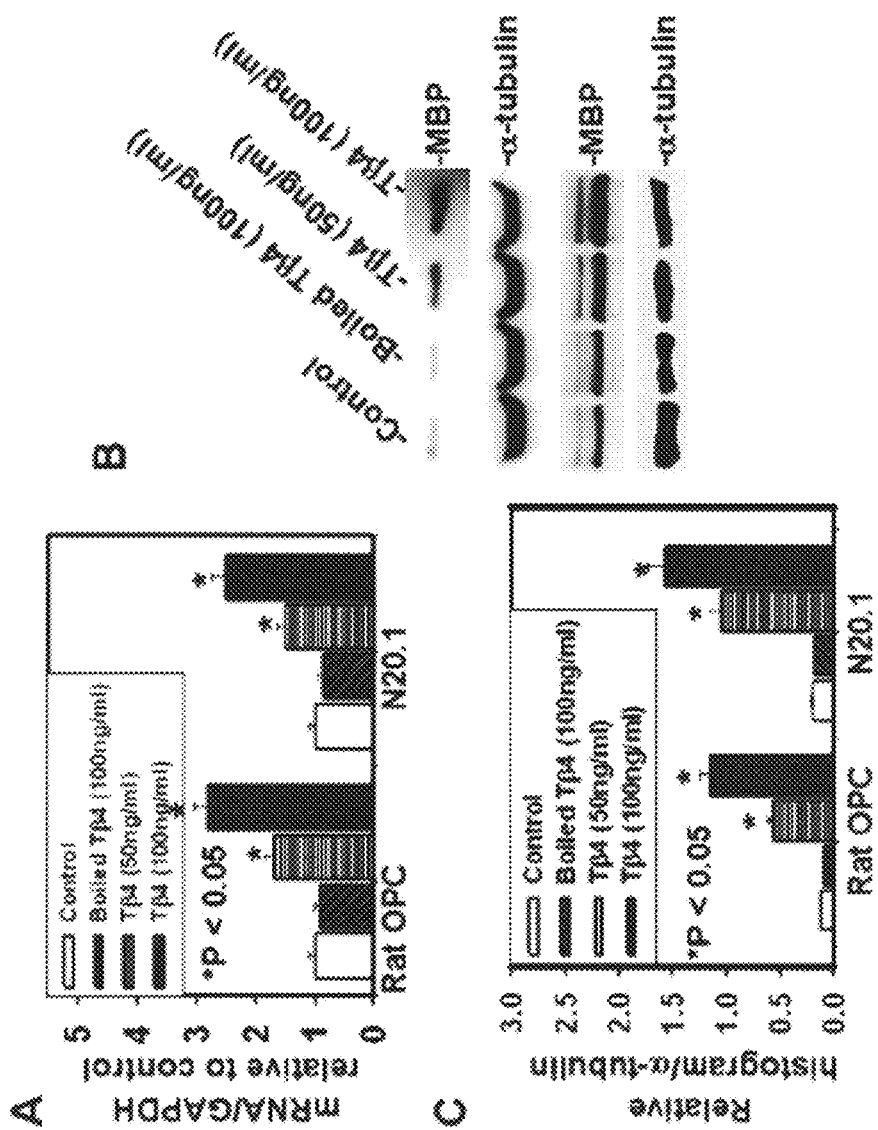
FIG. 11 is comprised of images and data representations showing application of LPS inhibitor polymyxin B for analysis of MBP expression after T34 treatment to test for confounding factor LPS contamination in Tβ4.

We also discovered that the effect of Tβ4 on the oligodendrocyte differentiation marker MBP is independent on LPS contamination in Tβ4. To avoid confounding data because of possible LPS contamination in Tβ4, OPC and N20.1 cells were cultured in the presence of polymyxin B (50 μg/ml) followed by Tβ4 treatment at the dose of 50 and 100 ng/ml for 4 days. The qrtPCR data indicate that Tβ4 treatment induced the expression of MBP in a dose-dependent manner even in the presence of polymyxin B (50 μg/ml) in rat OPC and N20.1 cells in both mRNA and protein levels (FIGS. 11A, B & C). In contrast, the boiled denatured Tβ4 (100 ng/ml) treatment had no effect on MBP expression (FIGS. 11A, B & C). FIG. 11 shows the results of application of LPS inhibitor polymyxin B for analysis of MBP expression after Tβ4 treatment to test for confounding factor LPS contamination in Tβ4. The total RNA and protein samples were prepared from primary rat (n=3) embryonic OPCs and mouse OPC cell line—N20.1 which were cultured in presence of polymyxin B (50 μg/ml) followed by the treatment with Tβ4 at the dose of 50 and 100 ng/ml in three independent experiments. Bar graph (A) indicates relative mRNA expression in compared to control for MBP in primary rat embryonic OPCs and mouse N20.1 cells. The protein samples were analyzed by Western Blot (B). Loading of samples shown at the top were normalized with α-tubulin. Migrations of proteins were shown at right. The protein bands in Western blot were quantified based on histogram analysis in compared to α-tubulin in Bar graph (C). $P<0.05$ was considered as significant. These data indicate that induction of MBP was solely dependent on natural Tβ4 and independent of LPS contamination.

Figure 12:
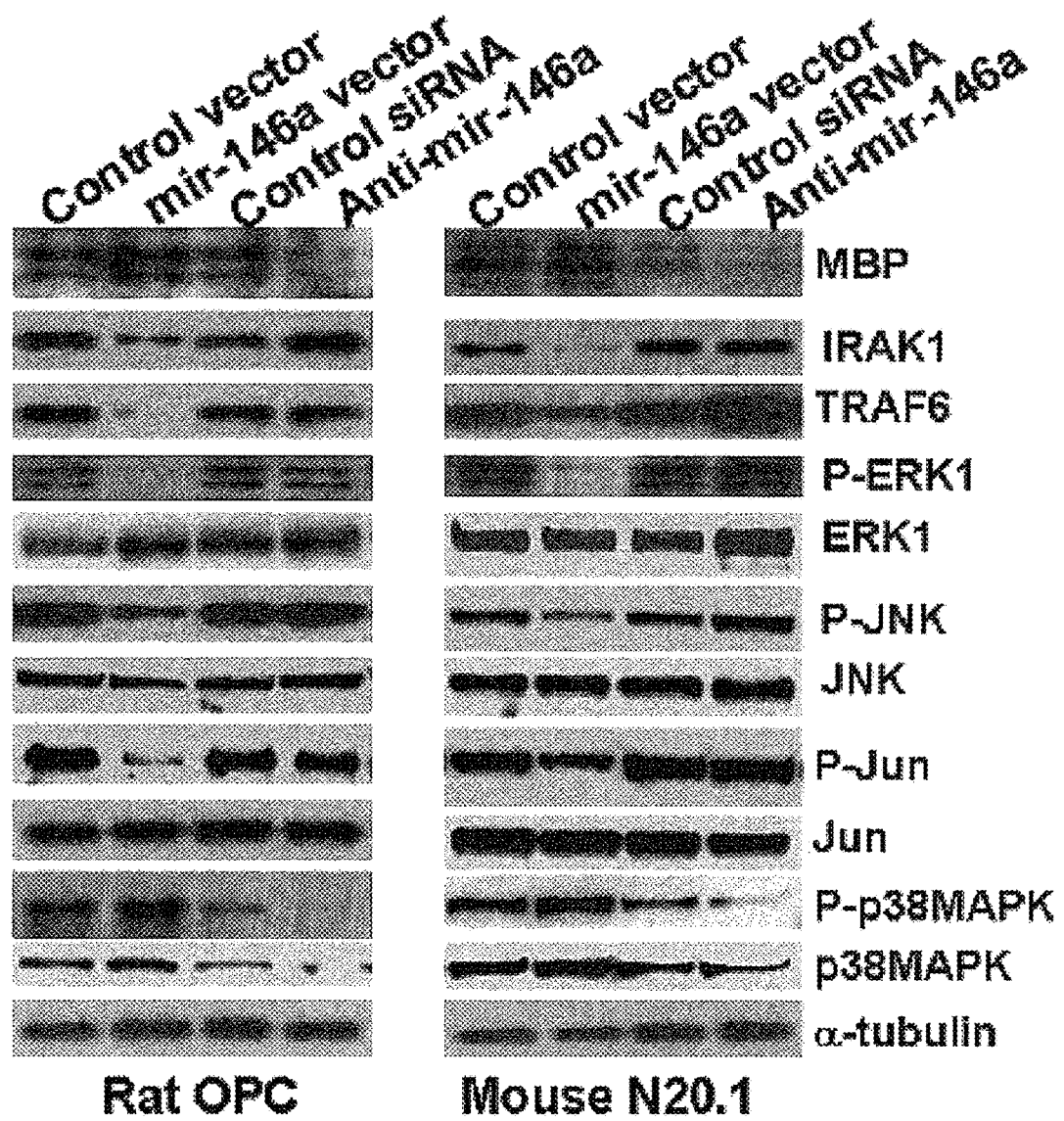
FIG. 12 is comprised of images showing the effect of miR-146a and anti-miR-146a transfection on downstream signaling mediators of TLR.

We also determined the effect of miR-146a and anti-miR-146a on downstream signaling mediators of TLR and MAPKs. We measured protein expression of IRAK1, TRAF6 and MAPKs in miR-146a overexpressing and miR-146a knockdown primary rat embryonic OPCs (n=3) and mouse N20.1 cells (n=3) (FIG. 12). Overexpression and knockdown of miR-146a were determined by quantitative analysis of miR-146a. After miR-146a transfection, miR-146a increased 51±5.3 fold in N20.1 cells and increased 33.5±4.1 fold in rat OPCs. A decrease of 73.1±8.3 fold in N20.1 cells and 46.7±5.2 fold in rat OPCs was observed for miR-146a knockdown. Western blot analysis revealed that the miR-146a transfection inhibited expression of IRAK1 and TRAF6 and increased expression and activation of p38MAPK. In contrast, transfection with anti-miR-146a inhibitor nucleotides significantly inhibited the expression of MBP and phosphorylation of p38MAPK (FIG. 12). Expression of IRAK1, TRAF6, p-ERK1, p-JNK and p-c-Jun remained unchanged or slightly elevated. These data indicate that miR-146a may be directly involved in OL differentiation by activation of the p38MAPK signaling pathway in rat primary embryonic OPCs and mouse N20.1 cells. FIG. 12 is comprised of images showing the effect of miR-146a and anti-miR-146a transfection on downstream signaling mediators of TLR. The primary rat embryonic OPCs (left panel) and mouse OPC cell line—N20.1 (right panel) were transfected with control pcDNA3 vector, miR-146a expression (pcDNA3) vector, control siRNA (Ambion) containing a random mixture of oligonucleotides for nucleotide control as a control for anti-miR-146a nucleotides (shown at the top) and were lysed for protein extraction and Western blot analysis. The loading of the samples were normalized with α-tubulin. Migrations of proteins are shown at right.

We also found that Tβ4 regulates miR-146a expression. To investigate the mechanistic link between Tβ4 and miR-146a on MBP expression, we further investigated the effect of both Tβ4 and miR-146a on the TLR signaling pathways using primary rat embryonic OPCs (n=3) and the mouse OPC cell line N20.1 (n=3).

Figure 13:
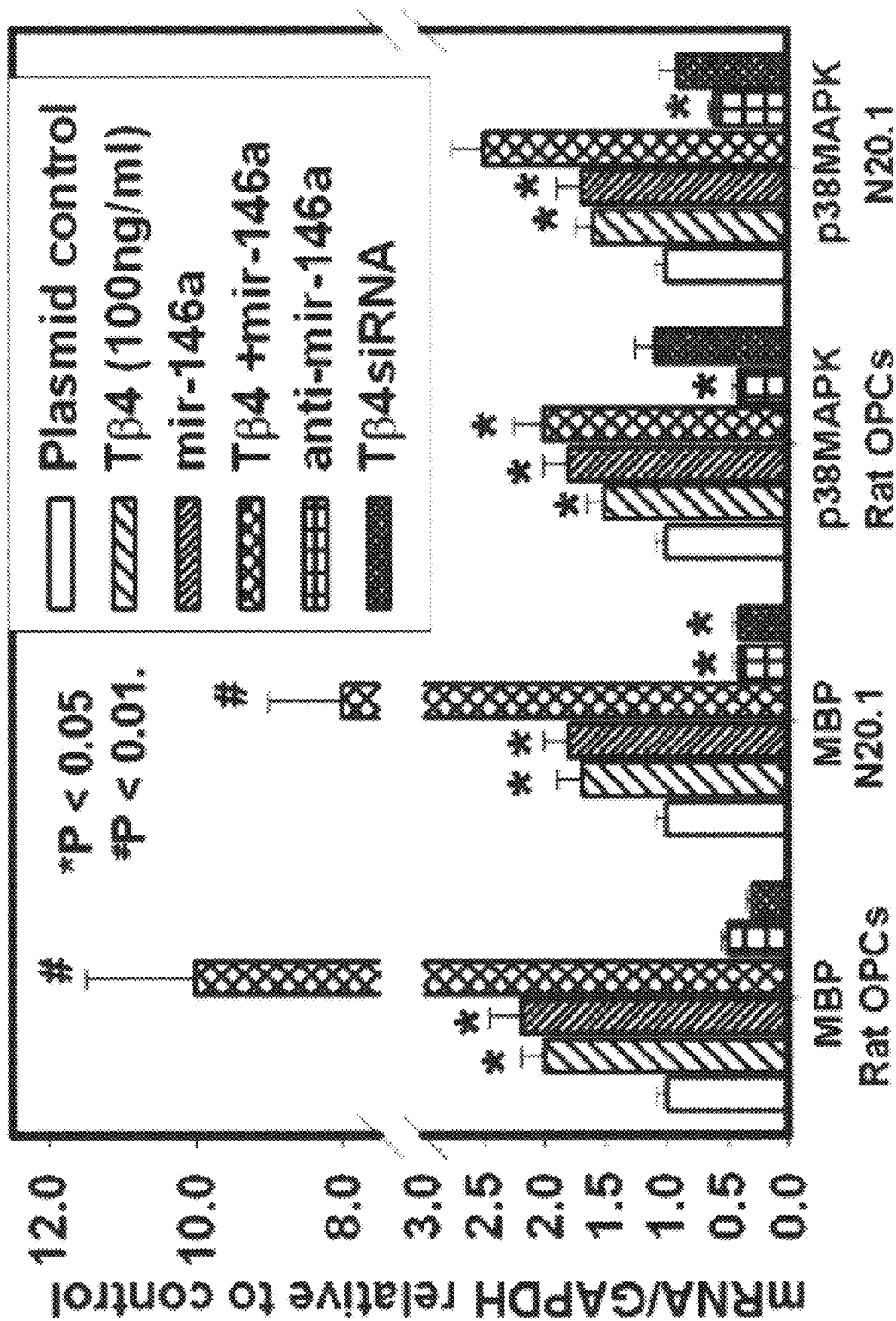
FIG. 13 is comprised of a data representation showing QrtPCR analysis of MBP and p38MAPK in OPCs.

FIG. 13 shows the results of QrtPCR analysis of MBP and p38MAPK in OPCs. QrtPCR analysis of MBP and p38MAPK was performed in total RNA samples extracted from the following transfected primary rat embryonic OPCs (Rat OPCs) and mouse OPC cell line—N20.1 (shown at bottom). These cells were transfected with control plasmid (plasmid control) and miR-146a vector (miR-146a transfection) followed by treatment without and with Tβ4 (100 ng/ml) (miR-146a+Tβ4). These OPCs were also transfected with anti-miR-146a (anti-miR-146a) and Tβ4siRNA. $P<0.05$ was considered as significant. FIG. 13 demonstrated a two-fold increase in mRNA MBP expression in the miR-146a transfection and Tβ4 group in rat primary embryonic OPCs and mouse N20.1 cells. However, a 10-fold increase in mRNA MBP expression was observed when miRR-146a transfected cells were grown in the presence of Tβ4, suggesting that Tβ4 amplifies miR-146a induced MBP expression. A similar but less robust result was observed when measuring p38MAPK.

Figure 14:
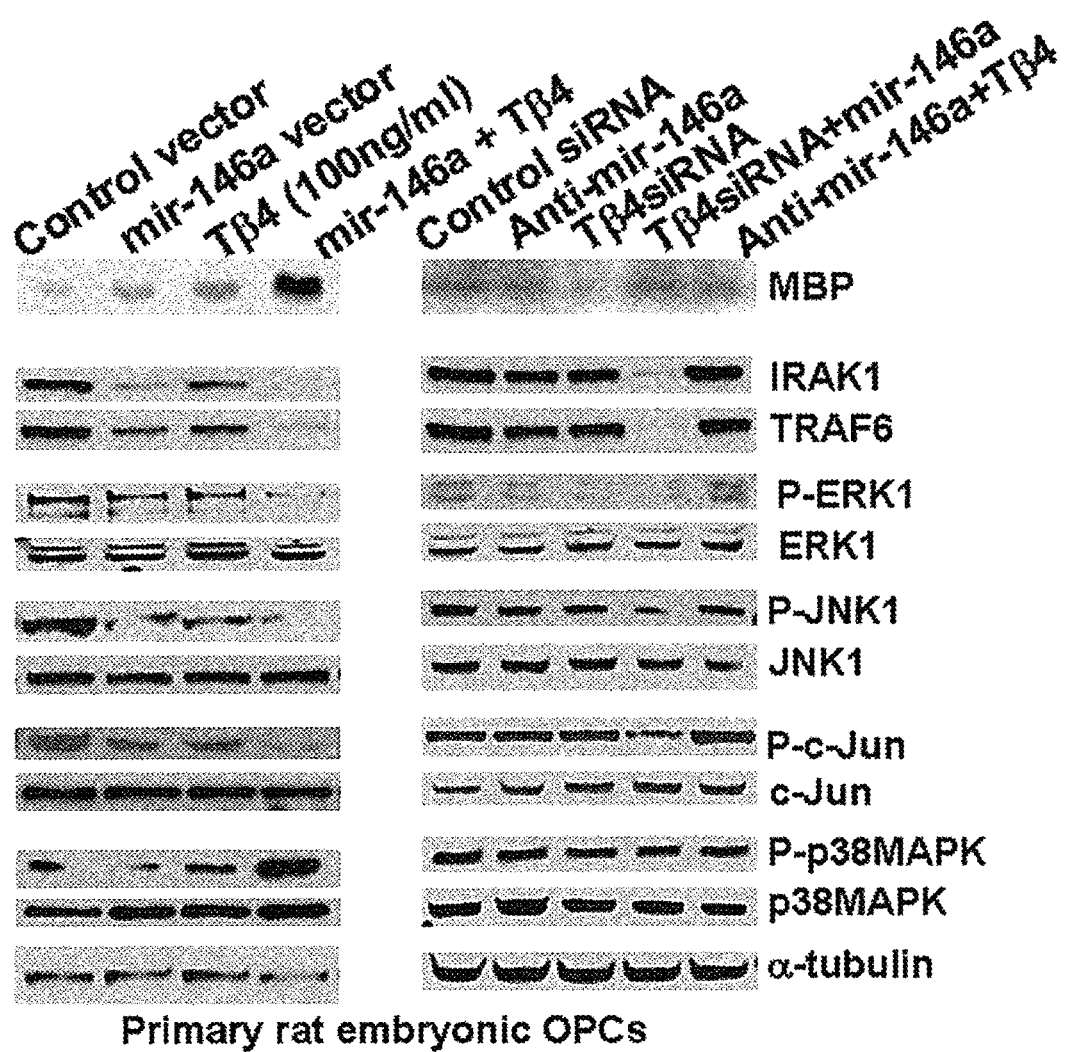
FIG. 14 is comprised of images showing the effect of Tβ4 treatment and transfection with miR-146a, anti-miR-146a and Tβ4siRNA on MBP expression and downstream signaling mediators of TLR in primary rat embryonic OPCs.

FIG. 14 shows the effect of Tβ4 treatment and transfection with miR-146a, anti-miR-146a and Tβ4siRNA on MBP expression and downstream signaling mediators of TLR in the primary rat embryonic OPCs: In the left panel, the primary rat embryonic OPCs were transfected with control pcDNA3 vector (Control vector), miR-146a expression vector (miR-146a vector), control pcDNA3 vector followed by Tβ4 treatment (Tβ4 100 ng/ml) and miR-146a expression vector followed by Tβ4 (100 ng/ml) treatment (miR-146a+Tβ4) (shown at the top). In the right panel, the primary rat embryonic OPCs were transfected with control siRNA, anti-miR-146a, Tβ4siRNA, Tβ4siRNA+miR-146a and anti-miR-146a followed by Tβ4 (100 ng/ml) treatment (anti-miR-146a+Tβ4) (shown at the top). These cells were lysed for protein extraction and Western blot analysis. The loading of the samples were normalized with α-tubulin. Migrations of proteins are shown at right. MiR-146a transfection combined with Tβ4 treatment markedly induced MBP expression in the OPCs. Tβ4 treatment failed to induce MBP expression in the absence of miR-146a as well as miR-146a transfection has no effect on MBP expression in Tβ4 negative OPCs.

Figure 15:
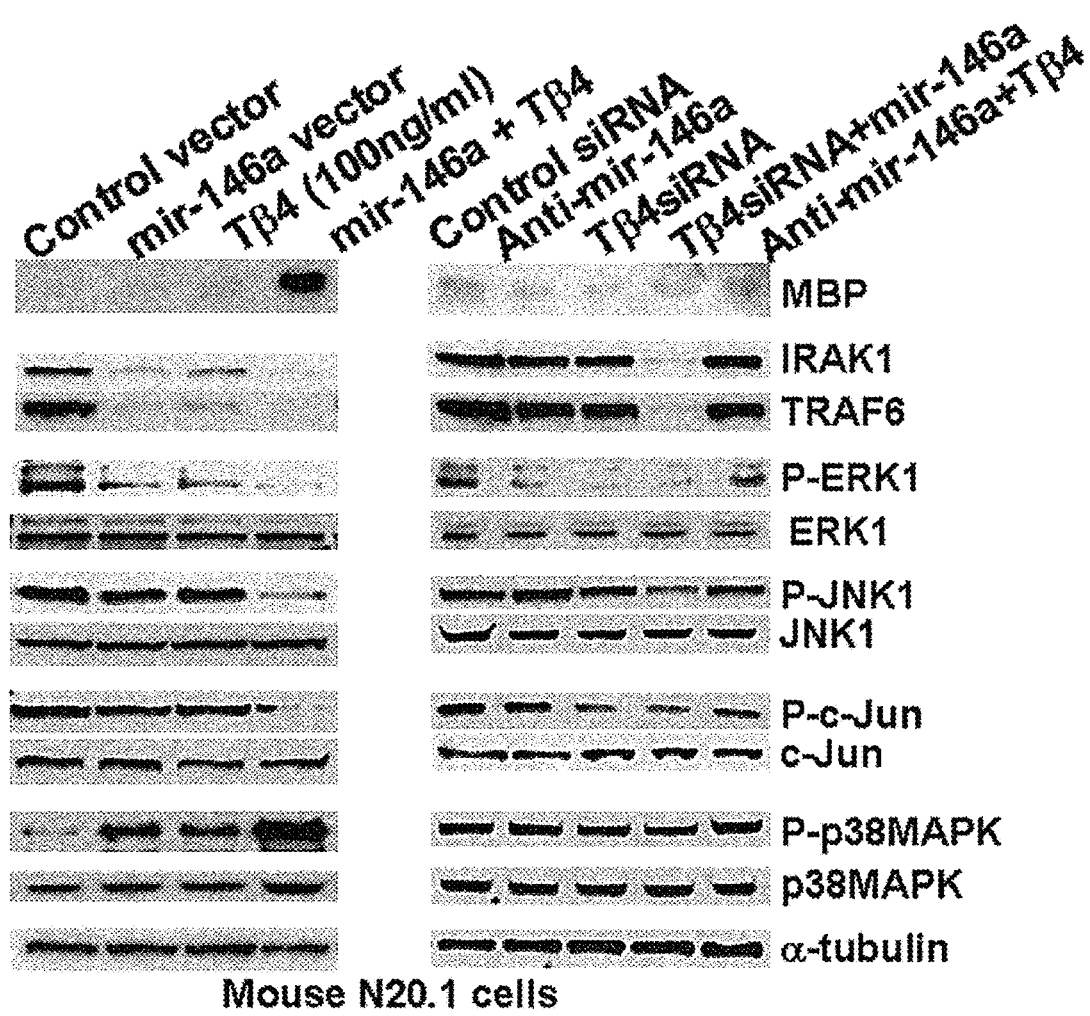
FIG. 15 is comprised of images showing Western blot analysis of MBP and downstream signaling mediators of TLR after Tβ4 treatment and transfection with miR-146a, anti-miR-146a and Tβ4siRNA in the mouse OPC cell line-N20.1.

FIG. 15 shows the results of Western blot analysis of MBP and downstream signaling mediators of TLR after Tβ4 treatment and transfection with miR-146a, anti-miR-146a and Tβ4siRNA in the mouse OPC cell line—N20.1: The left panel indicates N20.1 cells transfected with control pcDNA3 vector (Control vector), miR-146a expression vector (miR-146a vector), control pcDNA3 vector followed by Tβ4 treatment (Tβ4 100 ng/ml) and miR-146a expression vector followed by Tβ4 (100 ng/ml) treatment (miR-146a+Tβ4) (shown at the top). The right panel indicates N20.1 cells transfected with control siRNA, anti-miR-146a, Tβ4siRNA, Tβ4siRNA+miR-146a and anti-miR-146a followed by Tβ4 (100 ng/ml) treatment (anti-miR-146a+Tβ4) (shown at the top). The loading of the samples were normalized with α-tubulin. Migrations of proteins are shown at right. Note that marked induction of MBP was observed after miR-146a transfection combined with Tβ4 treatment in N20.1. Notice that either Tβ4 treatment or miR-146a transfection had no effect on MBP expression in the absence of miR-146a or Tβ4 in N20.1 cells.

Figure 16:
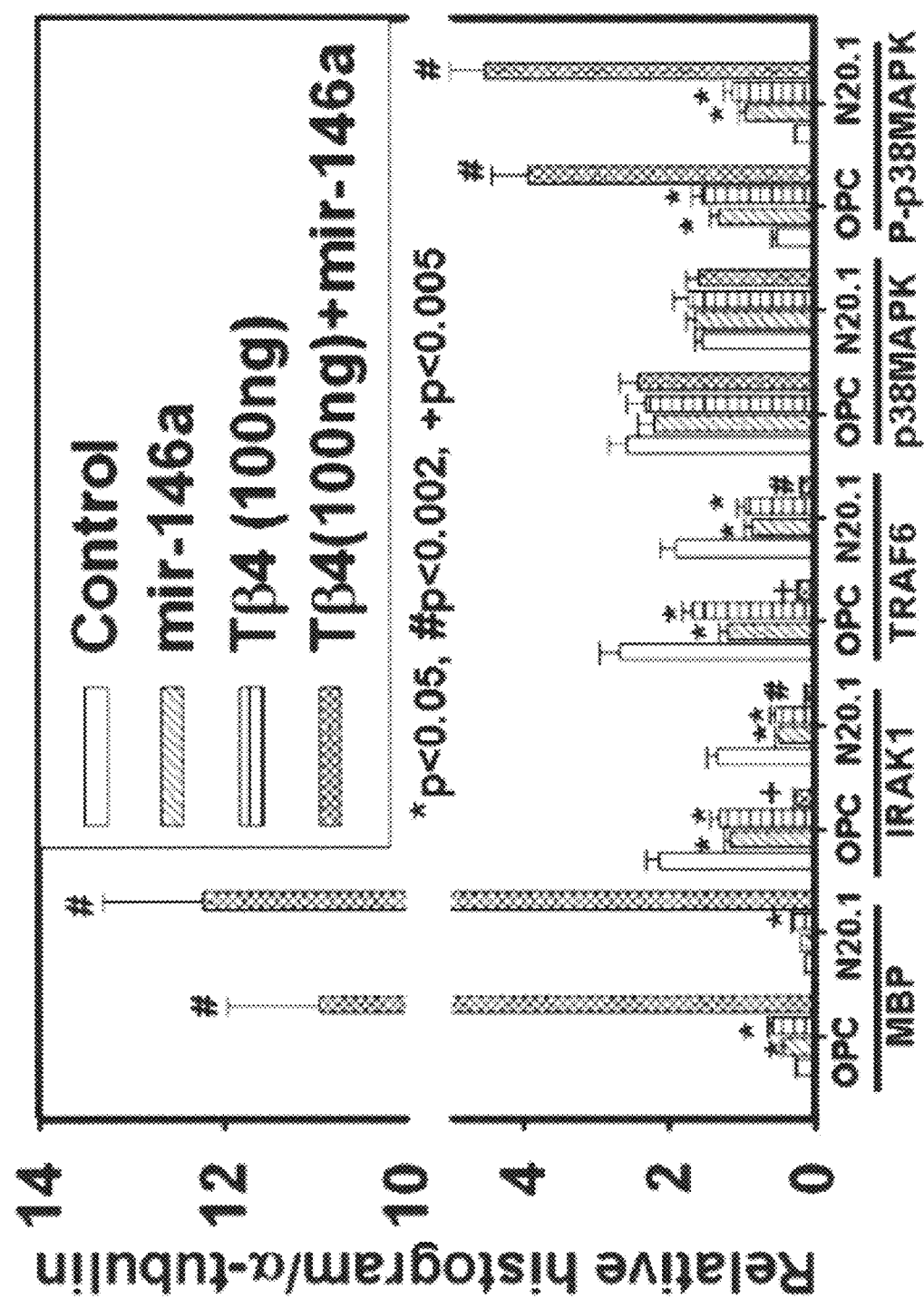
FIG. 16 is comprised of data representation showing quantitative analysis of expression of MBP, IRAK1, TRAF6, p38MAPK and phosphorylated P-p38MAPK at the protein level.

Western blot demonstrated similar results at the protein level as shown in FIG. 14 (primary rat OPCs) and FIG. 15 (mouse N20.1 cells). Furthermore, knockdown of miR-146a or silencing of Tβ4 using Tβ4siRNA (transfection efficiency of Tβ4siRNA was 58.3±6.2 fold in rat OPCs and 75.1±7.9 fold in N20.1 cells) inhibited MBP expression with no effect on the proinflammatory expression of IRAK1 and TRAF6 or the MAPKs, p-ERK1, p-JNK1 and p-c-Jun when compared with control (FIGS. 14 and 15). Silencing Tβ4 using Tβ4siRNA in miR-146a overexpressing cells showed inhibition of IRAK1 and TRAF6 without an increase of MBP expression suggesting that Tβ4 may be necessary for MBP expression. In contrast, knockdown of miR-146a cells treated with Tβ4 showed no change in the expression of MBP, IRAK1, TRAF6, p38 MAPK p-ERK1, p-JNK1, and p-c-Jun. These data indicate that miR-146a is a necessary component for Tβ4 mediated MBP expression. A histogram summarizing the protein expressions of MBP, IRAK1, TRAF6 and p38 MAPK in miR-146 overexpressed cells treated with Tβ4 is shown in FIG. 16. FIG. 16 shows the results of quantitative analysis of expression of MBP, IRAK1, TRAF6, p38MAPK and phosphorylated p38MAPK (P-p38MAPK) at the protein level. Western blot data from the primary rat embryonic OPCs (OPC) and mouse OPC cell line—N20.1 (N20.1) transfected with control vector and miR-146a expression vector followed by treatment with/without Tβ4 (100 ng/ml) were quantified based on histogram analysis in compared to α-tubulin. Bar graph indicates relative protein expression in compared to α-tubulin (at left) for MBP, IRAK1, TRAF6, p38MAPK and phosphorylated p38MAPK (P-p38MAPK) (at bottom) in primary rat embryonic OPCs and mouse N20.1 cells.

Collectively, these results indicate that Tβ4 promotes MBP expression through upregulation of miR-146a.

Figure 17:
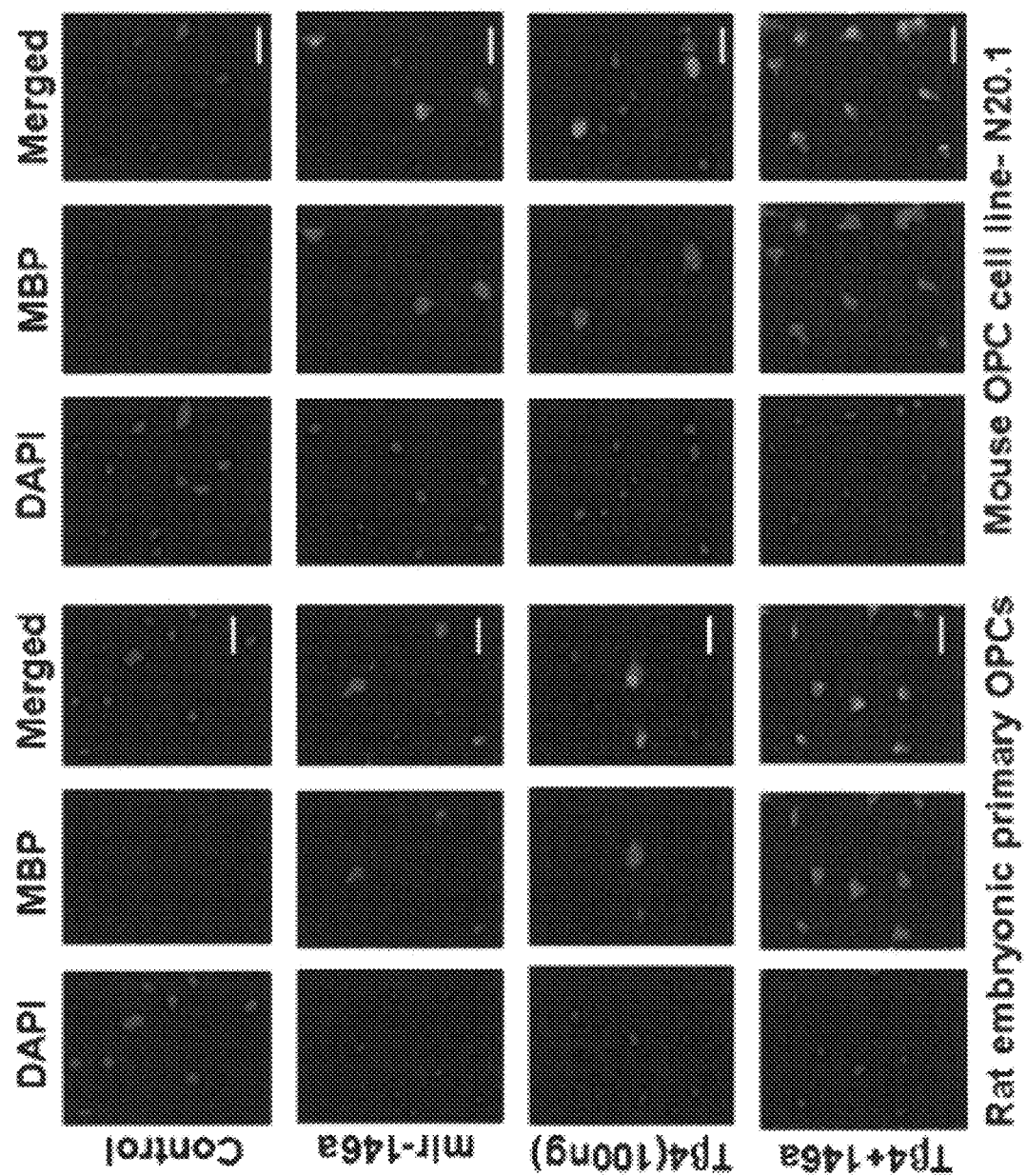
FIG. 17 is comprised of images showing immunohistochemistry of MBP in primary rat embryonic OPCs mouse N20.1 cells.
Figure 18:
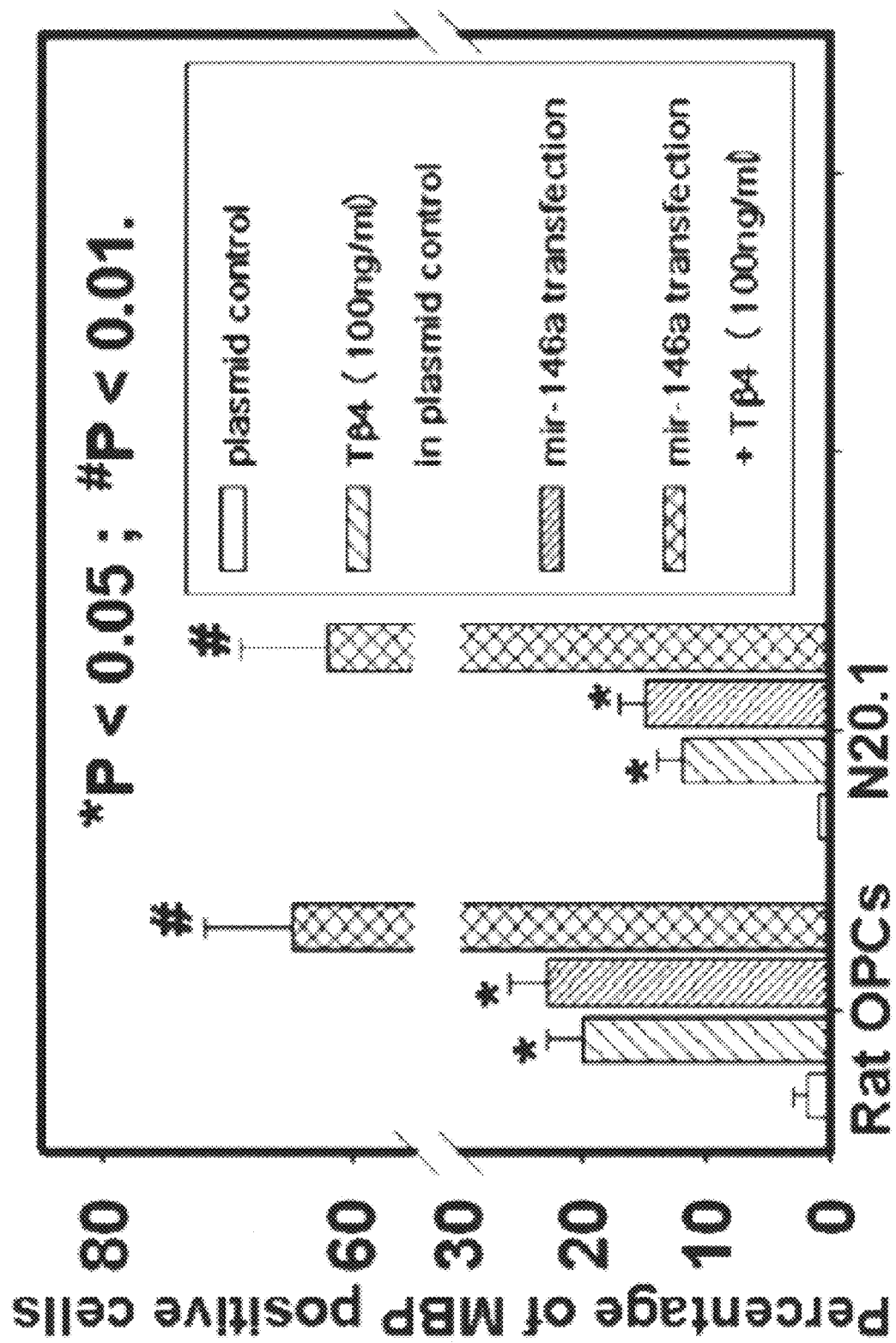
FIG. 18 is comprised of data representations showing quantitative analysis of MBP positive cells in primary rat embryonic OPCs and mouse N20.1 cells.

We also discovered unexpectedly that Tβ4 treatment and miR-146a transfection induces differentiation of OPC to mature oligodendrocytes. Rat primary embryonic OPCs and mouse N20.1 cells (n=3) were transfected with control (mock) and miR-146a vector, and treated with and without Tβ4 (100 ng/ml). The OPCs were immunofluorescently stained with antibodies against MBP and counter-stained with DAPI. These data were quantified by counting the number of MBP positive cells. DAPI positive cells were considered as the total number of cells. FIG. 17 shows immunohistochemistry of MBP in primary rat embryonic OPCs mouse N20.1 cells. The primary rat embryonic OPCs (left panel) and N20.1 cells (right panel) were transfected with control vector (control), control cells treated with Tβ4 (100 ng/ml) (Tβ4 (100 ng/ml)). Similarly, OPCs were also transfected with miR-146a (miR-146a) and miR-146a transfected cells treated with Tβ4 (100 ng/ml) (Tβ4+146a). The cells were immunofluorescence stained with Cy3 labeled antibody against OL marker—MBP and counterstained with DAPI. Images are merged (Merged). FIG. 18 shows the results of quantitative analysis of MBP positive cells in primary rat embryonic OPCs and mouse N20.1 cells. Primary rat embryonic OPCs and mouse N20.1 cells were transfected with control vector (control) and miR-146a vector (miR-146a transfection) followed by treated without and with Tβ4 (Tβ4 (100 ng/ml) and miR-146a transfection+ Tβ4 (100 ng/ml)). MBP positive cells after immunofluorescence staining were quantified by cell counting. Bar graph indicates percentage of MBP positive cells in primary rat embryonic OPCs and mouse N20.1 cells when DAPI positive cells was considered as 100% i.e. total number of cells. P<0.05 was considered as significant. The number of MBP positive OPCs was significantly increased after treatment with Tβ4 or transfection with miR-146a in rat primary embryonic OPCs and mouse N20.1 cells (FIGS. 17 and 18, respectively. The miR-146a transfection amplified the effect of Tβ4 treatment on MBP immunostaining of both sets of OPCs. These data suggest that Tβ4 treatment and miR-146a transfection induced OL differentiation in both rat primary embryonic OPCs and mouse N20.1 cells.

In our work, we discovered unexpectedly that Tβ4 regulates miR-146a and further indicates that Tβ4 mediates oligodendrogenesis. Our data demonstrate that Tβ4 increases expression of miR-146a in rat primary OPCs and mouse N20.1 OPCs, attenuates expression of IRAK and TRAF6, and reduces expression of phosphorylation/activation of ERK1, JNK1 and c-Jun, a negative regulator of MBP. Therefore, our data indicate that Tβ4 mediated oligodendrogenesis results from miR-146a suppression of the TLR proinflammatory pathway and modulation of the p38 MAPK pathway.

The innate immune system is an evolutionary primitive immediate responsive defensive strategy that responds to pathogens by pattern recognition, and in contrast to the adaptive immune system, does not confer long lasting immunity. The innate immune system orchestrates short term responses to tissue injury resulting from proteins released by damaged or dying cells. TLRs are activated by numerous ligands from bacterial or viral pathogens, however, oxidized proteins, matrix proteins and cell adhesion proteins also activate the innate system contributing to disease processes such as atherosclerosis and acute coronary syndromes. Inflammation initiates tissue repair after injury, however, it must be highly regulated so as not to harm the healing or recovering tissue. Negative regulation of the innate immune system is achieved by several proteins and miRs. MiR-146a, is an important negative regulator of the innate immune system, and it is also found to be highly expressed in developing oligodendrocytes during differentiation. Therefore, our finding that Tβ4 upregulates miR-146a in our in vitro models of OPCs in conjunction with previous observations that Tβ4 promotes recovery after neurological injury suggest a multipurpose role of Tβ4 in promoting oligodendrocyte differentiation as well as modulating the inflammatory response of the innate immune system by downregulating two components of the pathway, IRAK1 and TRAF6.

Without limitation to any particular mechanism of action, the observation that miR-146 is highly expressed in oligodendrocyte lineage cells indicates that maturation of oligodendrocytes occurs in an environment in which chronic inflammation is downregulated. Our results showing that Tβ4 increases expression of miR-146a while promoting differentiation of OPCs to MBP positive oligodendrocytes, support this. Inhibiting miR-146a in Tβ4 treated cells removed the inhibitor effect on the expression of IRAK and TRAF6 with no increase in MBP, expression suggesting that the miR-146a is a necessary component for MBP expression and downregulation of the TLR proinflammatory pathway. Moreover, overexpression of miR-146a in Tβ4 treated cells showed an amplified MBP expression and well as suppression of IRAK and TRAF6.

Our finding of Tβ4 modulation of the two key proinflammatory cytokines, IRAK and TRAF6 with corresponding down regulation of the expression of phosphorylation/activation of ERK1, JNK1 and c-Jun indicates that Tβ4 reduces inflammation, modulates the MAPKs and creates an environment for oligodendrocyte differentiation. Our work demonstrates similar results in rat primary OPCs, indicated that Tβ4 regulation of the MAPKs promotes oligodendrocyte differentiation. Furthermore, our data indicate that upregulation of miR-146a influences activation of p38 MAPK and corresponding suppression of ERK1 and JNK1, and thus promotes differentiation of OPCs to mature MBP oligodendrocytes.

In summary, we have discovered unexpectedly that Tβ4 treatment upregulates miR-146a expression in rat primary embryonic OPCs and mouse N20.1 cells. Tβ4 treatment induced miR-146a suppression of the proinflammatory cytokines IRAK1 and TRAF6 leading to upregulation of p38MAPK and inhibition of p-c-Jun, a negative regulator of MBP promoter. Tβ4 regulates miR-146a and may be required for MBP expression. These results provide further support for the therapeutic use of Tβ4 to mediate oligodendrogenesis as a treatment for neurological injury, damage, or disease.

Thus, without limitation and without waiver or disclaimer of embodiments or subject matter, some embodiments provide methods, systems, and compositions which provide, increase, or promote miRNA-146a and provide, increase, or improve neuronal differentiation, oligodendrocyte differentiation, and/or neurological outcome or function in treated subjects. Some embodiments comprise administration of a composition comprising a pharmaceutically effective amount of one or more of microRNA-146a, a promoter of microRNA-146a expression, exosomes containing or enriched in microRNA 146a, a microRNA-146a mimic, thymosin beta 4, and a phosphodiesterase 5 inhibitor (the above referred to convenience only as "miR-146a-related composition(s)" or "miR-146a-related composition administration") to prevent, control, or alleviate neurological conditions, disease, or injuries in subjects needing such treatment. In accordance with some embodiments, without limitation, one may inhibit such illness or injury through miR-146a-related composition administration for a finite interval of time, thereby limiting the development or course of such condition, disease or injury.

In accordance with some embodiments, there is a high likelihood that the duration of therapy comprising miR-146a-related composition administration would be relatively brief and with a high probability of success. Prophylactic miR-146a-related composition administration of some embodiments may greatly reduce the incidence of damage associated with some forms of illness or injury.

Any appropriate routes of miR-146a-related composition administration known to those of ordinary skill in the art may comprise some embodiments.

MiR-146a-related compositions of some embodiments would be administered and dosed in accordance with good medical practice, taking into account the clinical condition of the individual patient, the site and method of administration, scheduling of administration, patient age, sex, body weight and other factors known to medical practitioners. In accordance with some embodiments, experience with dose levels in animals is known and dose levels acceptable for safe human use are determinable or scalable in accordance with such information and/or good medical practice. The "pharmaceutically effective amount" for purposes herein is thus determined by such considerations as are known in the art. The amount must be effective to achieve improvement, including but not limited to, decrease in damage or injury, or improvement or elimination of symptoms and other indicators as are selected as appropriate measures by those skilled in the art.

In accordance with some embodiments, miR-146a-related compositions can be administered in various ways. They can be administered alone or as an active ingredient in combination with pharmaceutically acceptable carriers, diluents, adjuvants and vehicles. The miR-146a-related compositions can be administered orally, subcutaneously or parenterally including intravenous, intraarterial, intramuscular, intraperitoneal, and intranasal administration as well as intrathecal and infusion techniques, or by local administration or direct inoculation to the site of disease or pathological condition. Implants of the miR-146a-related compositions may also be useful. The patient being treated is a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active components of some embodiments. In some embodiments, miR-146a-related compositions may be altered by use of antibodies to cell surface proteins or ligands of known receptors to specifically target tissues of interest.

Since the use of miR-146a-related composition administration in accordance with some embodiments specifically targets the evolution, expression, or course of associated conditions or pathologies, it is expected that the timing and duration of treatment in humans may approximate those established for animal models in some cases. Similarly, the doses established for achieving desired effects using such compounds in animal models, or for other clinical applications, might be expected to be applicable in this context as well. It is noted that humans are treated generally longer than the experimental animals exemplified herein which treatment has a length proportional to the length of the disease process and drug effectiveness. The doses may be single doses or multiple doses over periods of time. The treatment generally has a length proportional to the length of the disease process and drug effectiveness and the patient species being treated.

In some embodiments, subjects, for example a human subject, having a neurological disease, disorder, condition or injury, may be treated with a composition comprising exosomes containing miR-146a. In some embodiments, the subject is administered exosomes containing miR-146a derived from naïve cells that are capable of producing miR-146a containing exosomes, for example, stem cells, (for example, a pluripotent stem cell, for example, an embryonic stem cell; an induced pluripotent stem cell; a hair follicle stem cell; a hematopoietic stem cell; a very small embryonic like stem cell, a mesenchymal stem cell; an endometrial regenerative cell (ERC); or a progenitor cell), mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes. In some embodiments, cells recited above that are capable of producing miR-146a containing exosomes are further genetically manipulated to express additional or higher amounts of miR-146a, (by transfecting cells transiently or stably with vectors or polynucleotides encoding miR-146a or complementary sequences thereof) as these exosomes are said to be "enriched" in miR-146a microRNA.

When administering the miR-146a-related compositions parenterally, in some embodiments, the composition may be formulated in a unit dosage injectable form (solution, suspension, or emulsion). The pharmaceutical formulations suitable for injection (for example, I.V. or I.P.) include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

When necessary, proper fluidity can be maintained, for example, by the use of a coating such as lecithin, by the maintenance of the required size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for such miR-146a-related composition compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to some embodiments, however, any vehicle, diluent, or additive used would have to be compatible with the miR-146a-related compositions.

Sterile injectable solutions can be prepared by incorporating miR-146a-related compositions utilized in practicing the some embodiments in the required amount of the appropriate solvent with various of the other ingredients, as desired.

A pharmacological formulation of some embodiments may be administered to the patient in an injectable formulation containing any compatible carrier, such as various vehicle, adjuvants, additives, and diluents; or the inhibitor(s) utilized in some embodiments may be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

In some embodiments, without limitation, the miR-146a-related compositions may be administered initially by intravenous injection to bring blood levels of miR-146a to a suitable level. The patient's levels of miR-146a are then maintained by injection, infusion or IV dosage forms comprising exosomes of the present invention, although other forms of administration, dependent upon the patient's condition and as indicated above, can be used. The quantity to be administered and the timing of administration may vary for the patient being treated. In some embodiments, the frequency of dosing can be determined by a physician or clinician using standard dosing methods known in the art. For example, the subject may be given an initial dosage that differs from later maintenance dosage forms. In some embodiments, the subject may be administered a first dose, and then the second and subsequent doses may be adjusted up or down in accordance with various factors, for example, the subject's tolerance to the administered doses, the overall effect provided by the last dose, the presence or absence of adverse side effects, the severity of the neurological disease, condition, disorder or injury and other factors known in the art. Generally speaking, one or more doses may be administered per day, or per week, or per month, with intervals ranging from 1 day to about 7 days, to about 14 days, or to about 30 days.

In various embodiments, exemplary compositions of the invention can be delivered to the subject at a dose that is effective to treat and/or prevent a neurological disease, disorder, condition or injury. The effective dosage will depend on many factors including the gender, age, weight, and general physical condition of the subject, the severity of the pain, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, The Science and Practice of Pharmacy ($21^{st}$ ed. 2005)). In one embodiment, the amount of miR-146a present in the exosomes administered to the subject in need thereof can range from about 0.1 to about 10.0 mg/m$^2$ surface area of the patient, e.g., about 0.6 to about 4.0 mg/m$^2$, about 1.0 to about 3.0 mg/m$^2$, or about 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 mg/m$^2$. In some instances, the dose can be even lower, e.g., as low as 0.1, 0.05, 0.01, 0.005, or 0.001 mg/m$^2$ or lower. In some instances, the dose can be even higher, e.g., as high as 20, 50, 100, 500, or 1000 mg/m$^2$ or higher. The present invention encompasses every sub-range within the cited ranges and amounts.

In some embodiments, the compositions comprising exosomes containing miR-146a of the invention may be administered at doses ranging from about $1 \times 10^1$ to about $1 \times 10^{15}$ exosomes per kg body weight of the patient, or about $1 \times 10^3$ to about $1 \times 10^{14}$ exosomes per kg body weight of the patient, or about $1 \times 10^3$ to about $1 \times 10^{13}$ exosomes per kg body weight of the patient, or about $1 \times 10^3$ to about $1 \times 10^{12}$ exosomes per kg body weight of the patient, or about $1 \times 10^3$ to about $1 \times 10^{11}$ exosomes per kg body weight of the patient, or about $1 \times 10^3$ to about $1 \times 10^{10}$ exosomes per kg body weight of the patient, or about $1 \times 10^3$ to about $1 \times 10^9$ exosomes per kg body weight of the patient, or about $1 \times 10^3$ to about $1 \times 10^8$ exosomes per kg body weight of the patient, or about $1 \times 10^3$ to about $1 \times 10^7$ exosomes per kg body weight of the patient, or from about $1 \times 10^3$ to about $1 \times 10^6$ exosomes per kg body weight of the patient, or from about $1 \times 10^7$ to about $1 \times 10^{15}$ exosomes per kg body weight of the patient, or from about $1 \times 10^7$ to about $1 \times 10^{14}$ exosomes per kg body weight of the patient, or from about $1 \times 10^7$ to about $1 \times 10^{13}$ exosomes per kg body weight of the patient, or from about $1 \times 10^7$ to about $1 \times 10^{12}$ exosomes per kg body weight of the patient.

In some embodiments, a subject in need of treatment can be administered with a dose of about $1 \times 10^7$ to about $1 \times 10^{15}$ exosomes per dose, or per day, or as a bolus. Preferably, the exosomes (containing or enriched in miR-146a) containing composition or formulation of the invention is administered at a dose of about $1 \times 10^9$ to about $1 \times 10^{15}$ exosomes per kg body weight of the patient, or a dose (a therapeutically effective dose, or a daily dose, or a weekly dose) of about $1 \times 10^{10}$ to about $5 \times 10^{13}$ exosomes for an average adult weighing approximately 70 kg.

In various embodiments, the exemplified doses of exosomes per kg weight of the patient are daily doses or therapeutically effective doses, either in unit form or in sub-unit forms to be dosed one or more times per day. In various embodiments, each of these daily doses or therapeutically effective doses, either in unit form or in sub-unit forms may be administered to a subject with a neurological disease, disorder, condition or injury in the form of parenteral administration, for example, intravenous (I.V.), intraperitoneal (I.P.), infusion, or stereotactically administered in the form of a liquid, for example, a solution, an emulsion, or a suspension containing the exosomes and one or more pharmaceutically acceptable excipients, carriers, or diluents.

In some embodiments, a subject with a neurological disease, injury, disorder or condition may be treated with a pharmaceutically effective amount of the exosomes of the present invention, for example, the subject may be administered with $1 \times 10^3$ to about $1 \times 10^{15}$ exosomes per dose, or per day, or as a bolus. In some embodiments, compositions of the present invention containing from about $1 \times 10^3$ to about $1 \times 10^{15}$ exosomes, can be administered parenterally to a subject in need thereof, once every two days, for about 1-4 weeks and then once per week, for the next 4 to about 52 weeks, or until a skilled physician or clinician determines that treatment can be discontinued, or until symptoms have resolved.

In some embodiments, patients with a neurological disease, injury or disorder, for example, a stroke or traumatic brain injury, or peripheral neuropathy and diabetic neuropathy patient, may be treated by administration of an initial or first dose of about $4 \times 10^{11}$-about $5 \times 10^{13}$ exosomes/kg body weight of the subject, delivered at 24 hours after injury.

Follow-on doses may range from about 5×10⁹ to about 5×10¹³ exosomes/kg body weight of the subject, 14 days after the initial dose, optionally with a single weekly dose of about 5×10⁹ to about 5×10¹³ exosomes per week thereafter until dosing is terminated. In some embodiments, multiple sclerosis patients may be treated by dosing 4×10¹¹ to about 5×10¹³ exosomes/kg body weight of the subject, twice weekly for about 1-8 weeks, preferably 1-4 weeks in duration.

Additionally, in some embodiments, without limitation, miR-146a-related compositions may be administered in situ to bring internal levels to a suitable level. The patient's levels are then maintained as appropriate in accordance with good medical practice by appropriate forms of administration, dependent upon the patient's condition. The quantity to be administered and timing of administration may vary for the patient being treated.

SEQUENCES

SEQ ID NO: 1:
MicroRNA-146a, described generally as:
UGAGAACUGAAUUCCAUGGGUU

SEQ ID NO: 2:
Thymosin beta 4, described generally as:
Ser-Asp-Lys-Pro-Asp-Met-Ala-Glu-Ile-Glu-Lys-Phe-
Asp-Lys-Ser-Lys-Leu-Lys-Lys-Thr-Glu-Thr-Gln-Glu-
Lys-Asn-Pro-Leu-Pro-Ser-Lys-Glu-Thr-Ile-Glu-Gln-
Glu-Lys-Gln-Ala-Gly-Glu-Ser

SEQ ID NO: 3:
5T-TACTICGGCTGGITCCTGAC-3T 5T-

SEQ ID NO: 4:
5T-GCCTICCCGTAGICACAAAA-3T 5T

SEQ ID NO: 5:
ATGGCATCACAGAAGAGACCCTCA-3' 5T-

SEQ ID NO: 6:
TAAAGAAGCGCCCGATGGAGTCAA-3' 5T-

SEQ ID NO: 7:
ATGACGAAATGACCGGCTAC-3' 5T-

SEQ ID NO: 8:
ACAACGTTCTTCCGGTCAAC-3 5T-

SEQ ID NO: 9:
GCTGAACAAAGGGAGAGACG-3T 5T-

SEQ ID NO: 10:
TGCTTTCTCCCCAAATTGAC-3T 5T-

SEQ ID NO: 11:
TICAATGICCACAGATCCGA-3T 5'-

SEQ ID NO: 12:
CTAACCAATTCCCCATCCCT-3T 5T-

SEQ ID NO: 13:
GCCATTCTGGTAGAGGAAGTTTCTC-3' 5T-

SEQ ID NO: 14:
CGCCAGTCCAAAATCAAGAATC-3' 5T-

SEQ ID NO: 15:
TGAAGCAGAGCATGACCTTG-3' 5T-

SEQ ID NO: 16:
CACAAGAACTGAGTGGGGGT-3' 5T-

SEQ ID NO: 17:
CGCAACCAGTCAAGTTCTCA-3T

SEQUENCES

SEQ ID NO: 18:
GAAAAGTAGCCCCCAACCTC-3T

Example 3

Cerebral Endothelial Cell Exosomes Enriched in miR-146a for the Treatment of Neurological Diseases, Injuries, and Disorders To investigate the effect of miR-146a exosomes on diabetic neuropathy, male diabetic mice (db/db) at age of 20 weeks were treated once a week with miR-146a containing exosomes derived from mesenchymal stromal cells (MSCs) miR-146a exosomes (10¹⁰ exosomes/mouse, n=8/group) or saline for 4 consecutive weeks via a tail vein. Non-diabetic mice (dm) were employed as a negative control group. Behavioral tests and electrophysiological tests (sensory and motor nerve conduction velocity) were performed once a week or every two weeks, respectively. The animals were sacrificed 8 weeks after the initial administration.

Figure 19:
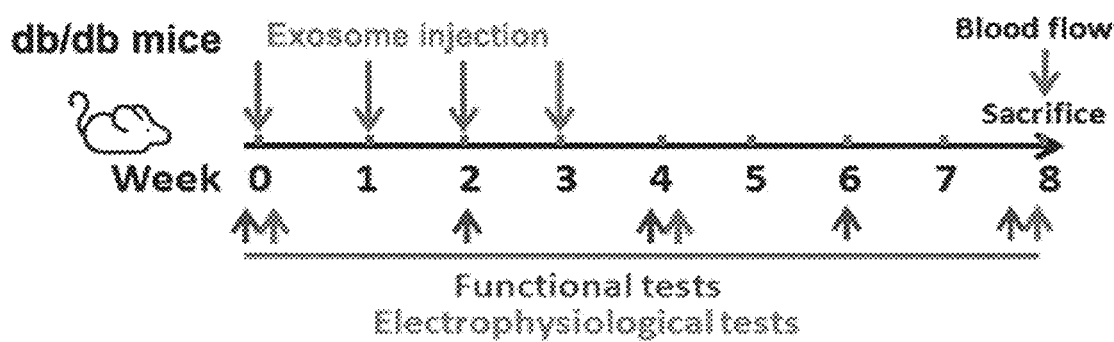
FIG. 19 depicts a timescale for performing the experiments related to administration of miR-146a exosomes to treat diabetic neuropathy in male diabetic mice (db/db).
Figure 20A:
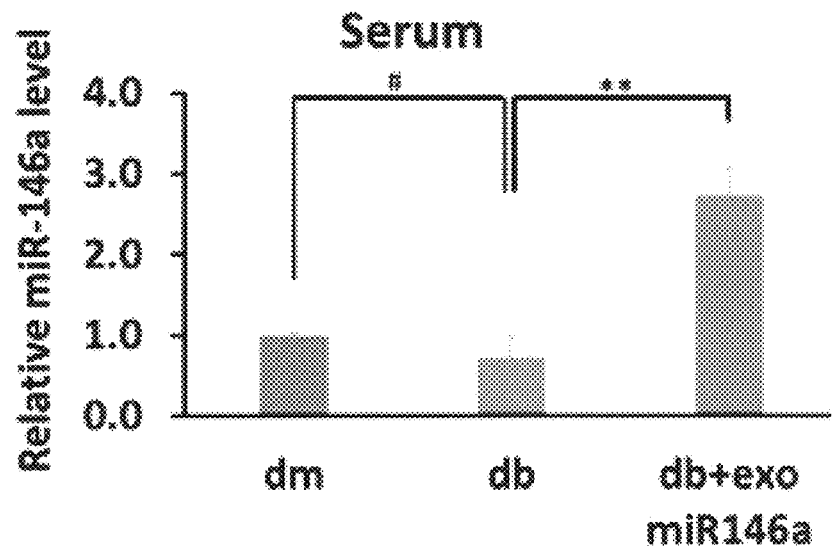
FIG. 20A depicts a bar graph illustrating results of real-time RT-PCR data showing levels of serum miR-146a in the treated and untreated animals.
Figure 20B:
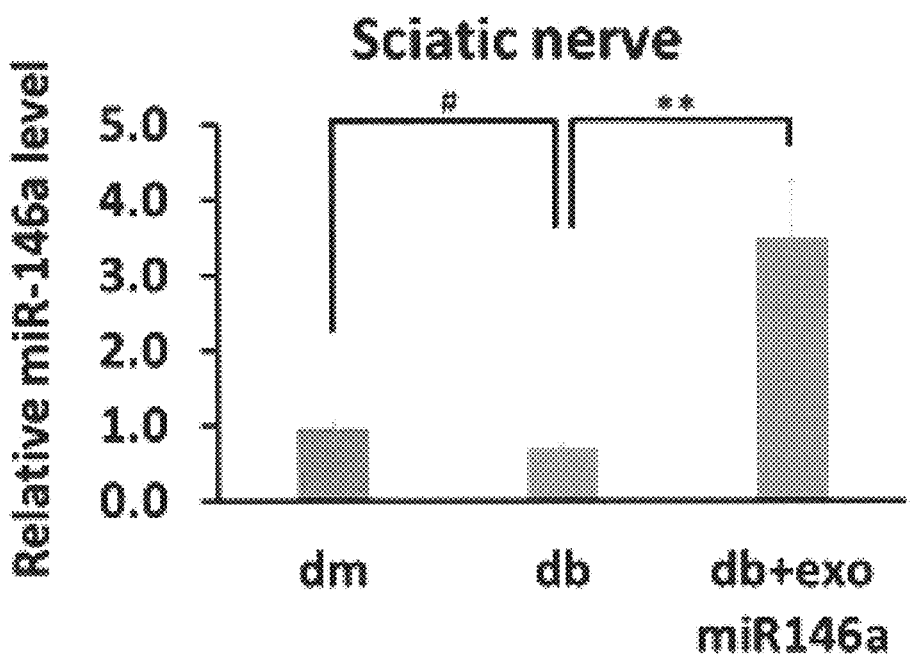
FIG. 20B depicts a bar graph illustrating results of real-time RT-PCR data showing levels of sciatic nerve miR-146a in the treated and untreated animals.

The inventors of the present disclosure examined whether administration of tailored miR-146a exosomes affects miR-146a levels in diabetic animals using a dosing regimen shown in FIG. 19. Sciatic nerve tissues and blood sera were collected 24 hours after the last treatment. Quantitative real-time RT-PCR data show levels of miR-146a were decreased in sera (FIG. 20A) and sciatic nerves (FIG. 20B) of diabetic mice compared with tissues of non-diabetic (dm) mice. However, db/db (db) mice treated with tailored miR-146a-exosomes displayed significant elevation of miR-146a levels (db+exo miR-146a). N=3/group. #P<0.05 vs control dm mice, **p<0.01 vs diabetic mice treated with saline.

Figure 21A:
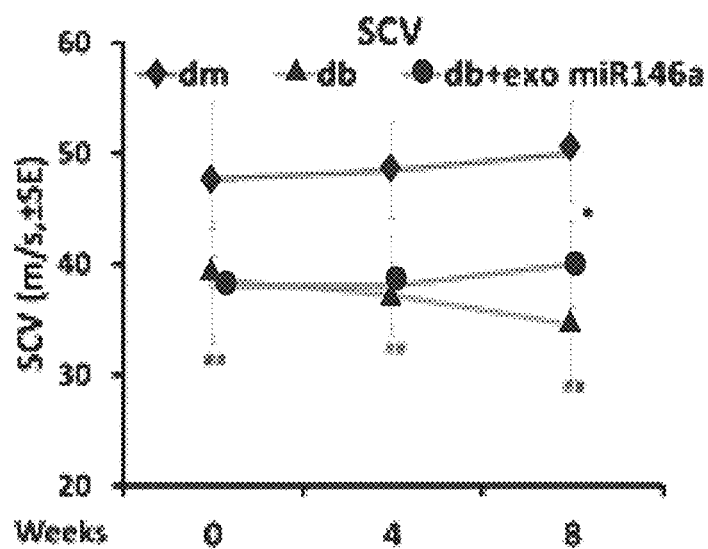
FIG. 21A depicts a line graph illustrating the effect of exosomes containing miR-146a microRNA on the sciatic nerve conduction velocity in treated and untreated animals.
Figure 21B:
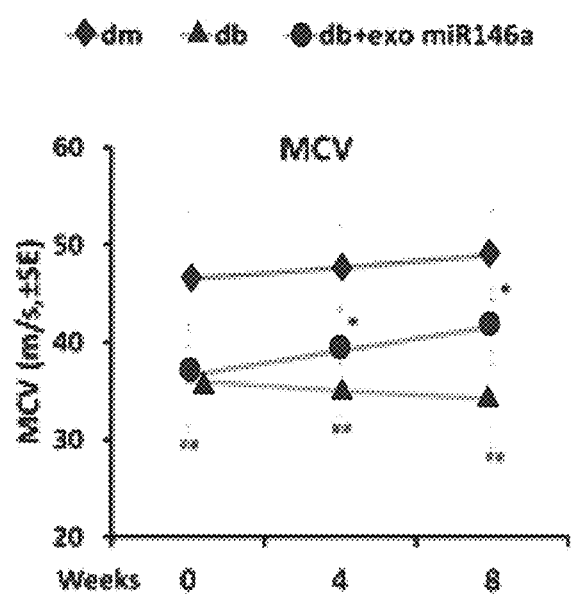
FIG. 21B depicts a line graph illustrating the effect of exosomes containing miR-146a microRNA on the thermal hyperalgesia effects induced in treated and untreated diabetic mice.
Figure 21C:
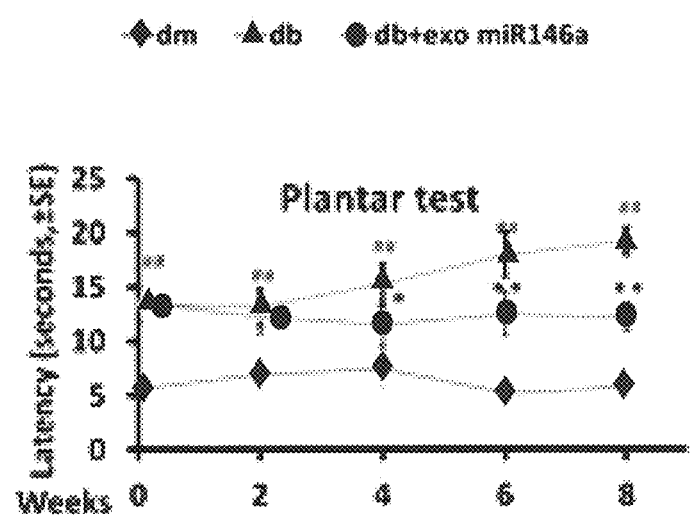
FIG. 21C depicts a line graph illustrating the effect of exosomes containing miR-146a microRNA on the tactile allodynia effects in diabetic mice.

Next, the inventors examined the effect of miR-146a-exosomes on neurological function including electrophysiological tests, thermal hyperalgesia and tactile allodynia measurements in diabetic mice. Sciatic nerve conduction velocity (FIG. 21A) was examined using orthodromic recording techniques. To examine the sensitivity of mice to heat, plantar test was done using a thermal stimulation meter. As shown above in FIGS. 21B and 21C, we found that exosomes had a statistically significant positive impact on each of these measures at various times after administration.

Figure 22A:
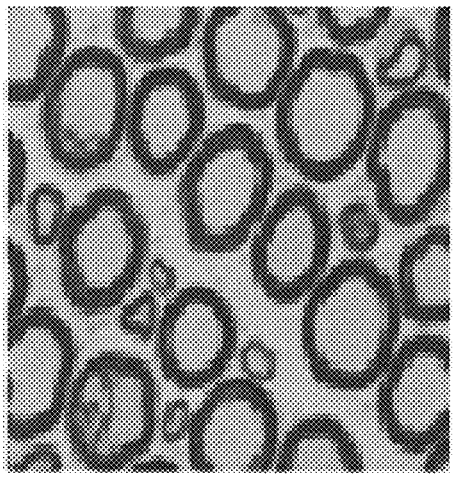
FIG. 22A depicts semi-thin toluidine blue-stained transverse sections of sciatic nerves derived from non-diabetic mice (dm).
Figure 22B:
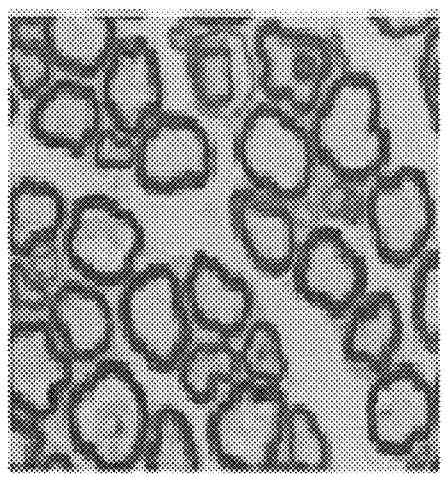
FIG. 22B depicts semi-thin toluidine blue-stained transverse sections of sciatic nerves derived from diabetic mice (db) treated with saline.
Figures 22C, 22D:
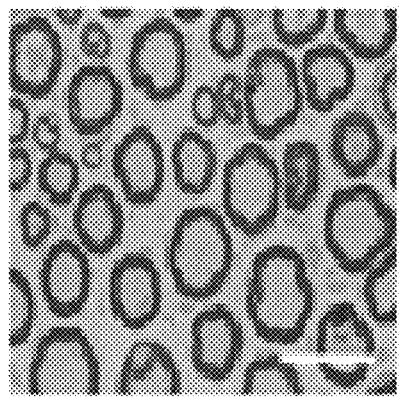
FIG. 22C depicts semi-thin toluidine blue-stained transverse sections of sciatic nerves derived from diabetic mice treated with miR-146a microRNA containing exosomes.
FIG. 22D depicts a table providing quantitative data of histomorphometric parameters of sciatic nerves from diabetic and non-diabetic mice treated or untreated with miR-146a microRNA containing exosomes.

We next measured the impact of miR-146a exosomes on myelin thickness in the sciatic nerve. Representative images of semi-thin toluidine blue-stained transverse sections of sciatic nerves derived from non-diabetic (dm, FIG. 22A), diabetic mice treated with saline (db, FIG. 22B) or diabetic mice treated with tailored miR-146a-exosomes (db+exo miR-146a, FIG. 22C). The quantitative data of histomorphometric parameters of sciatic nerves are shown in tabular form in FIG. 22D. These results showed that mean fiber and axon diameters as well as myelin sheath thickness were reduced in diabetic mice, nevertheless increased in tailored miR-146a-exosomes treated diabetic mice. Mean g-ratio was significantly increased in diabetic animals indicating mild hypomyelination whereas tailored miR-146a exosome treatment led to a significant increase of myelinated fiber density. Bar=50 μm. N=8/group.

Figure 23:
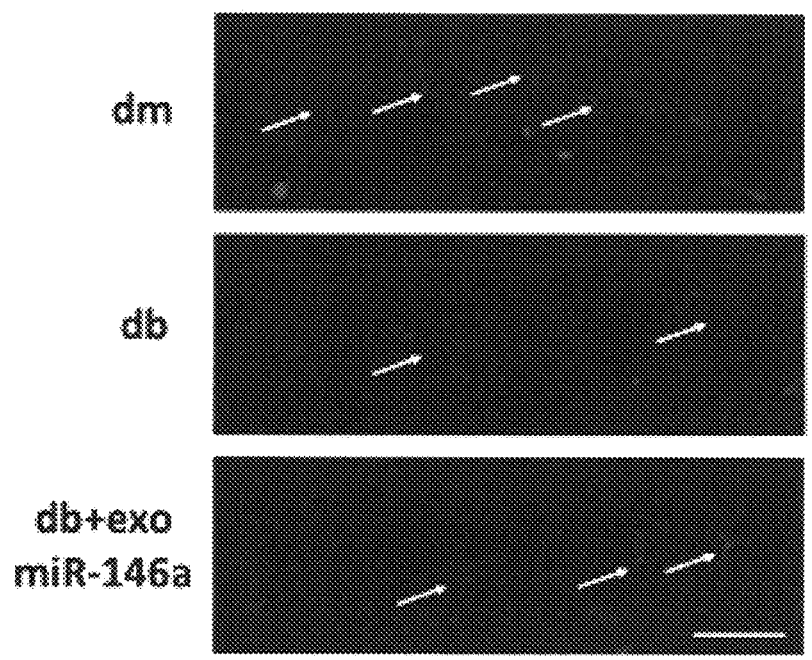
FIG. 23 depicts photomicrographs of intraepidermal nerve fibers (IENF) in skin of the foot-pads identified by the antibody against PGP9.5 of diabetic and non-diabetic mice treated or untreated with miR-146a microRNA containing exosomes.
Figure 24:
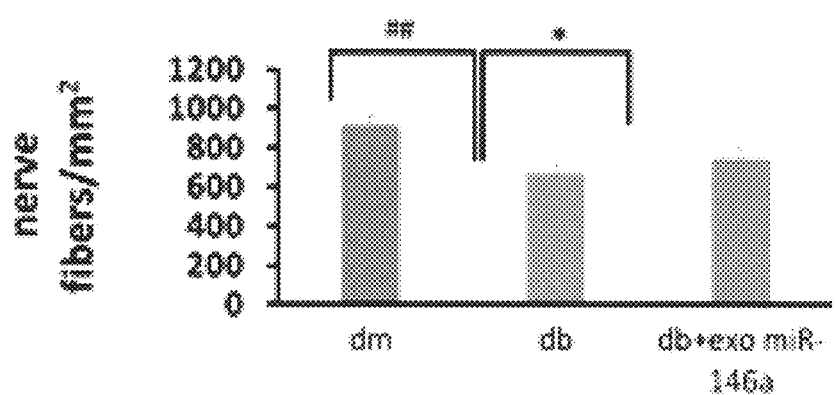
FIG. 24 depicts a bar graph depicting quantitative analysis of the effects of miR-146a microRNA containing exosomes on the number of PGP9.5 immunoreactive intraepidermal nerve fiber in diabetic mice (db+exo miR-146a) as shown in FIG. 23.

Compared to age matched non-diabetic db/m mice, db/db mice treated with saline showed approximately a 25% decrease in the number of intraepidermal nerve fibers (IENF) in skin of the foot-pads identified by the antibody against PGP9.5, which is a cytoplasmic ubiquitin C-terminal hydrolase expressed in all types of efferent and afferent peripheral nerve fibers. (See FIG. 23). In contrast, the treatment with tailored miR-146a-exosomes significantly increased PGP9.5 immunoreactive intraepidermal nerve fiber (arrows) in diabetic mice (db+exo miR-146a) by representative microscopic images and quantitative analysis as shown in FIG. 24. Bar=50 µm. ## P<0.01 versus the dm group, * P<0.05 versus db group. n=8/group.

Figure 25:
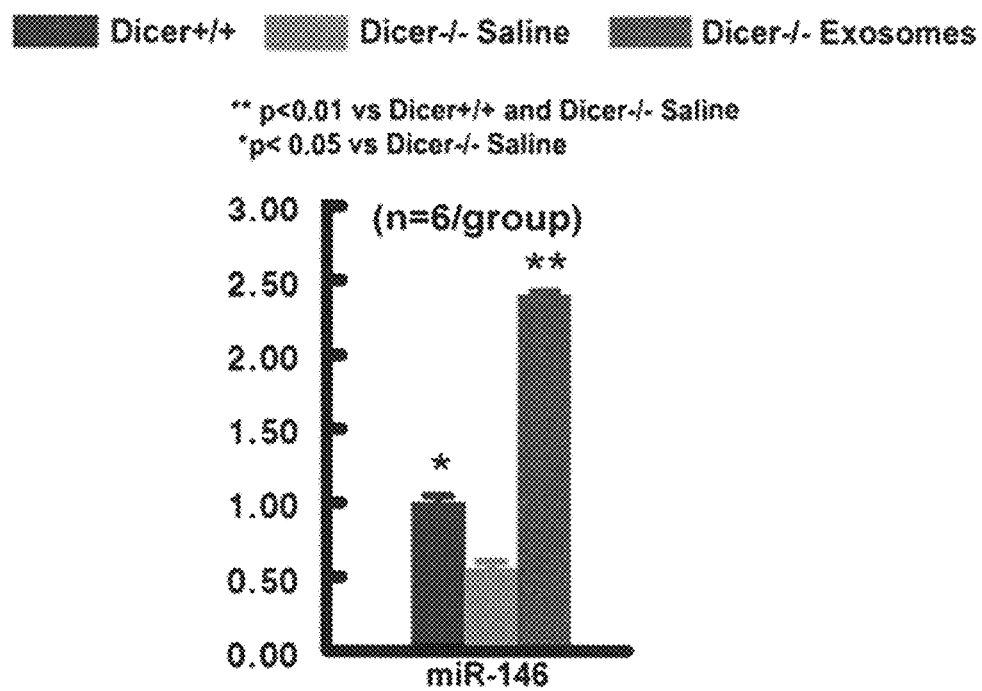
FIG. 25 depicts a bar graph representing levels of miR-146a microRNA after intranasal administration of cerebral endothelial cell derived exosomes ($1\times10^9$ particles/administration) in neural stem cells of Dicer knockout mice (n=10) compared to Dicer knockout mice treated with saline (n=12).

Dicer is essential for mature miRNA formation. Real-time RT-PCR analysis showed that ablation of Dicer in neural stem cells of adult mice (Adult Ascl1creER™/Dicer$^{fl/fl}$/Tomato$^{fl/fl}$ (Dicer−/−) led to significant reduction of miR-146a and among others compared to wild-type mice (Ascl1creER™/Tomato$^{fl/fl}$ (Dicer+/+) See FIG. 25). However, as shown in FIG. 25, intranasal administration of cerebral endothelial cell derived exosomes ($1 \times 10^9$ particles/administration) every other day for five times significantly increased miR-146a levels in neural stem cells of Dicer knockout mice (n=10) compared to Dicer knockout mice treated with saline (n=12).

While some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. It is intended that the following claims define the scope of the invention and that the methods, systems, and compositions within the scope of these claims and their equivalents be covered thereby. This description of some embodiments should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

What is claimed is:

1. A method of treating a subject suffering from a neurological disease or injury with exosomes containing miR-146a microRNA, comprising:
administering to the subject in need thereof, a therapeutically effective amount of the exosomes containing miR-146a microRNA to treat the subject with the neurological disease or injury.

2. The method of claim 1, wherein the exosomes are derived from one or more exosome producing cell populations comprising: stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes.

3. The method of claim 2, wherein the stem cells are selected from the group consisting of: progenitor cells; pluripotent stem cells; embryonic stem cells; induce pluripotent stem cells; hair follicle stem cells; hematopoietic stem cells; very small embryonic like stem cells; mesenchymal stem cells; endometrial regenerative cells (ERC); and neural progenitor cells.

4. The method of claim 1, wherein the exosomes are administered to the subject intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or stereotactically into neural tissue.

5. The method of claim 1, wherein the cell population is derived from the subject.

6. The method of claim 1, wherein the neurological disease or injury comprises stroke, brain injury, central pontine, dementia, multiple sclerosis (MS) (together with the similar diseases called idiopathic inflammatory demyelinating diseases), tumefactive multiple sclerosis, Solitary sclerosis, cognitive decline from aging, Alzheimer's disease, Parkinson's disease, epilepsy, migraine, neuropathy, for example, peripheral neuropathy, Vitamin B12 deficiency, myelinolysis, Tabes Dorsalis, transverse myelitis, Devic's neuromyelitis optica, fulminant or acute idiopathic inflammatory-demyelinating disease, Marburg variant of multiple sclerosis, Bal61s concentric sclerosis, Schilder's disease, acute disseminated encephalomyelitis; transverse myelitis, optic neuritis, progressive multifocal leukoencephalopathy, acute hemorrhagic leukoencephalitis, acute disseminated encephalomyelitis, anti-myelin oligodendrocyte glycoprotein autoimmuneencephalomyelitis, Leukodystrophy, adrenoleukodystrophy, adrenomyeloneuropathy, chronic inflammatory demyelinating polyradiculoneuropathy (CIDP), Guillain-Barre syndrome, chronic inflammatory demyelinating polyneuropathy, or anti-MAG peripheral neuropathy.

7. The method of claim 6, wherein the neurological disease or injury comprises dementia, traumatic brain injury, peripheral neuropathy, diabetic neuropathy, stroke or multiple sclerosis.

8. The method of claim 1, wherein the subject is administered with about $1 \times 10^7$ to about $1 \times 10^{15}$ exosomes per dose, or per day, or as a bolus.

9. A method of treating a subject suffering from a neurological disease or injury with cells capable of producing miR-146a microRNA, the method comprising:

providing a cell population capable of producing exosomes containing miR-146a; and administering to the subject in need thereof, the cell population capable of producing exosomes containing miR-146a microRNA in a pharmaceutically effective amount to treat the subject with respect to the neurological disease or injury.

10. The method of claim 9, wherein the cell population comprises: stem cells, mesenchymal stromal cells, umbilical cord cells, endothelial cells, Schwarm cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia; or mastocytes.

11. The method of claim 10, wherein the stem cells are selected from the group consisting of: embryonic stem cells; pluripotent stem cells; induced pluripotent stem cells; hair follicle stem cells; hematopoietic stem cells; very small embryonic like stem cells; mesenchymal stem cells; endometrial regenerative cells (ERC); and progenitor cells.

12. The method of claim 9, wherein the cell population is administered stereotactically in the brain.

13. The method of claim 9, wherein the neurological disease or injury comprises stroke, brain injury, central pontine, dementia, multiple sclerosis (MS) (together with the similar diseases called idiopathic inflammatory demyelinating diseases), tumefactive multiple sclerosis, Solitary sclerosis, cognitive decline from aging, Alzheimer's disease, Parkinson1s disease, epilepsy, migraine, neuropathy, for example, peripheral neuropathy, Vitamin B12 deficiency, myelinolysis, Tabes Dorsalis, transverse myelitis, Devic's neuromyelitis optica, fulminant or acute idiopathic inflammatory-demyelinating disease, Marburg variant of multiple sclerosis, Bal6's concentric sclerosis, Schilderls disease, acute disseminated encephalomyelitis; transverse myelitis, optic neuritis, progressive multifocal leukoencephalopathy, acute hemorrhagic leukoencephalitis, acute disseminated encephalomyelitis, anti-myelin oligodendrocyte glycoprotein autoimmune encephalomyelitis, Leukodystrophy, adrenoleukodystrophy, adrenomyeloneuropathy, chronic inflammatory demyelinating polyradiculoneuropathy (CIDP), Guillain-Barre syndrome, chronic inflammatory demyelinating polyneuropathy, or anti-MAG peripheral neuropathy.

14. The method of claim 13, wherein the neurological disease or injury comprises dementia, brain injury, peripheral neuropathy, stroke or multiple sclerosis.

15. A method of treating a subject suffering from dementia, brain injury, neuropathy, stroke or multiple sclerosis with exosomes containing miR-146a microRNA, the method comprising:

administering to the subject in need thereof, the exosomes containing miR-146a microRNA in a pharmaceutically effective amount to treat the subject with the dementia, brain injury, neuropathy, stroke or multiple sclerosis.

16. The method according to claim 15, wherein the exosomes are derived from cell populations genetically modified to produce miR-146a in amounts greater than nave unmodified cells.

17. The method of claim 15, wherein the exosomes are derived from one or more cell populations comprising: stem cells, mesenchymal stromal cells, umbilical cord cells, endothelial cells, Schwarm cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes.

18. The method of claim 17, wherein the stem cells are selected from the group consisting of: embryonic stem cells; pluripotent stem cells; induced pluripotent stem cells; hair follicle stem cells; hematopoietic stem cells; very small embryonic like stem cells; mesenchymal stem cells; endometrial regenerative cells (ERC); and progenitor cells.

19. The method of claim 15, wherein the exosomes are administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or directly into neural tissue.

20. A method of treating a subject suffering from stroke with exosomes containing miR-146a the method comprising:

administering to the subject in need thereof, the exosomes in a pharmaceutically effective amount to treat the subject with the stroke.

21. The method of claim 20, wherein the exosomes are derived from a cell population comprising: stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes.

22. The method of claim 21, wherein the stem cells are selected from the group consisting of: embryonic stem cells; pluripotent stem cells; induced pluripotent stem cells; hair follicle stem cells; hematopoietic stem cells; very small embryonic like stem cells; mesenchymal stem cells; endometrial regenerative cells (ERC); and progenitor cells.

23. The method of claim 20, wherein the exosomes are administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or directly into neural tissue.

* * * * *